(12) United States Patent
Bond et al.

(10) Patent No.: US 9,993,444 B2
(45) Date of Patent: Jun. 12, 2018

(54) USE OF BETA-ADRENERGIC INVERSE AGONISTS FOR SMOKING CESSATION

(75) Inventors: Richard A. Bond, San Francisco, CA (US); Mitchell Glass, Wilmington, DE (US)

(73) Assignee: INVION, INC., Seventeen Mile Rocks (AU)

( * ) Notice: Subject to any disclaimer, the term of this patent is extended or adjusted under 35 U.S.C. 154(b) by 111 days.

(21) Appl. No.: 13/978,845

(22) PCT Filed: Jan. 9, 2012

(86) PCT No.: PCT/US2012/020590
§ 371 (c)(1),
(2), (4) Date: Jul. 9, 2013

(87) PCT Pub. No.: WO2012/096866
PCT Pub. Date: Jul. 19, 2012

(65) Prior Publication Data
US 2013/0295025 A1 Nov. 7, 2013

Related U.S. Application Data

(60) Provisional application No. 61/431,308, filed on Jan. 10, 2011.

(51) Int. Cl.
| | |
|---|---|
| *A61K 31/138* | (2006.01) |
| *A61K 45/06* | (2006.01) |
| *A61K 31/403* | (2006.01) |
| *A61K 31/5377* | (2006.01) |
| *A61K 9/68* | (2006.01) |
| *A61K 9/70* | (2006.01) |

(52) U.S. Cl.
CPC .......... *A61K 31/138* (2013.01); *A61K 31/403* (2013.01); *A61K 31/5377* (2013.01); *A61K 45/06* (2013.01); *A61K 9/0058* (2013.01); *A61K 9/7023* (2013.01)

(58) Field of Classification Search
None
See application file for complete search history.

(56) References Cited

U.S. PATENT DOCUMENTS

| | | |
|---|---|---|
| 3,598,122 A | 8/1971 | Zaffaroni |
| 3,598,123 A | 8/1971 | Zaffaroni |
| 3,731,683 A | 5/1973 | Zaffaroni |
| 3,797,494 A | 3/1974 | Zaffaroni |
| 4,031,894 A | 6/1977 | Urquhart et al. |
| 4,144,317 A | 3/1979 | Higuchi et al. |
| 4,201,211 A | 5/1980 | Chandrasekaran et al. |
| 4,286,592 A | 9/1981 | Chandrasekaran |
| 4,314,557 A | 2/1982 | Chandrasekaran |
| 4,379,454 A | 4/1983 | Campbell et al. |
| 4,428,926 A | 1/1984 | Keith |
| 4,435,180 A | 3/1984 | Leeper |
| 4,559,222 A | 12/1985 | Enscore et al. |
| 4,568,343 A | 2/1986 | Leeper et al. |
| 4,573,995 A | 3/1986 | Chen et al. |
| 4,588,580 A | 5/1986 | Gale et al. |
| 4,645,502 A | 2/1987 | Gale et al. |
| 4,698,062 A | 10/1987 | Gale et al. |
| 4,704,282 A | 11/1987 | Campbell et al. |
| 4,725,272 A | 2/1988 | Gale |
| 4,764,382 A * | 8/1988 | Kydonieus ........... A61K 9/7084 424/434 |
| 4,781,924 A | 11/1988 | Lee et al. |
| 4,788,062 A | 11/1988 | Gale et al. |
| 4,816,258 A | 3/1989 | Nedberge et al. |
| 4,849,226 A | 7/1989 | Gale |
| 4,904,475 A | 2/1990 | Gale et al. |
| 4,908,027 A | 3/1990 | Enscore et al. |
| 4,917,895 A | 4/1990 | Lee et al. |
| 4,938,759 A | 7/1990 | Enscore et al. |
| 4,943,435 A | 7/1990 | Baker et al. |
| 5,004,610 A | 4/1991 | Osborne et al. |
| 5,071,656 A | 12/1991 | Lee et al. |
| 5,116,867 A | 5/1992 | Klein et al. |
| 5,122,382 A | 6/1992 | Gale et al. |
| 5,141,750 A | 8/1992 | Lee et al. |
| 5,284,660 A | 2/1994 | Lee et al. |
| 5,314,694 A | 5/1994 | Gale et al. |
| 5,342,623 A | 8/1994 | Enscore et al. |
| 5,411,740 A | 5/1995 | Lee et al. |
| 5,635,203 A | 6/1997 | Gale et al. |
| 6,039,980 A | 3/2000 | Baichwal |

(Continued)

FOREIGN PATENT DOCUMENTS

| | | |
|---|---|---|
| JP | 2007-527409 A | 9/2007 |
| WO | 2002024198 A1 | 3/2002 |

(Continued)

OTHER PUBLICATIONS

Bruijnzeel, A.W., et al. ("Effects of prazosin, clonidine, and propranolol on the elevations in brain reward thresholds and somatic signs associated with nicotine withdrawal in rats", Psychopharmacology (2010) 212:485-499).*

(Continued)

*Primary Examiner* — Isaac Shomer
*Assistant Examiner* — Michael P Cohen
(74) *Attorney, Agent, or Firm* — Ditthavong & Steiner, P.C.

(57) ABSTRACT

The chronic use of p-adrenergic inverse agonists such as nadolol, carvedilol, and ICI-118,551 provides an improved method for the treatment of mucus hypersecretion in subjects with such mucus hypersecretion. One aspect of a method according to the present invention is a method of preventing or controlling mucus hypersecretion in the respiratory tract comprising administering a therapeutically effective quantity of a p-adrenergic inverse agonist to a subject with mucus hypersecretion or at risk of mucus hypersecretion. The invention further encompasses pharmaceutical compositions comprising the p-adrenergic inverse agonist and the additional compound.

18 Claims, 6 Drawing Sheets

(56) References Cited

U.S. PATENT DOCUMENTS

| | | |
|---|---|---|
| 6,284,800 B1 | 9/2001 | Broder et al. |
| 6,551,989 B2 | 4/2003 | Nadel et al. |
| 6,740,634 B1 | 5/2004 | Saikawa |
| 2002/0086850 A1 | 7/2002 | Cox et al. |
| 2005/0080113 A1 | 4/2005 | Ohkawa et al. |
| 2006/0194882 A1 | 8/2006 | Bond |
| 2007/0032517 A1 | 2/2007 | Debenham et al. |
| 2008/0152709 A1* | 6/2008 | Bortz .................. A61K 9/209 424/457 |
| 2009/0325958 A1 | 12/2009 | Navratil et al. |
| 2010/0197719 A1 | 8/2010 | Bozung et al. |

FOREIGN PATENT DOCUMENTS

| | | | |
|---|---|---|---|
| WO | 2005034871 A2 | 4/2005 | |
| WO | WO 2005034871 A2 * | 4/2005 | ........... A61K 31/137 |

OTHER PUBLICATIONS

David R. Curran and Lauren Cohn. Advances in Mucous Cell Metaplasia: A Plug for Mucus as a Therapeutic Focus in Chronic Airway Disease. Am J Respir Cell Mol Biol vol. 42. pp. 268-275, 2010.*

Roger Dobson. Pill to make smokers forget their craving. Daily Mail, Jun. 23, 2009. Downloaded Aug. 25, 2015 from: http://www.dailymail.co.uk/health/article-1194773/Pill-make-smokers-forget-craving.html.*

J B M Mullen, J L Wright, B R Wiggs, P D Pare, J C Hogg. Structure of central airways in current smokers and ex-smokers with and without mucus hypersecretion: relationship to lung function. Thorax 1987;42:843-848.*

Samir Malhotra, S F Paul Man & Don D Sin. Emerging drugs for the treatment of chronic obstructive pulmonary disease. Expert Opin. Emerging Drugs (2006) 11(2):275-291.*

U.S. Department of HS. How Tobacco Smoke Causes Disease:the Biology and Behavioral Basis for Smoking-Attributable Disease: A Report of the Surgeon General. Atlanta, GA: U.S. Department of Health and Human Services, 2010, p. 329.*

N A Hanania, S Singh, R Eli-Wali, M Flashner, A E Franklin, W J Garner, B F Dickey, S Parra, S J Ruoss, F Shardonofsky, B J O'Connor, C Page, and R A Bond. The Safety and Effects of the Beta-Blocker, Nadolol, in Mild Asthma; An Open-label Pilot Study. Pulm Pharmacol Ther. 2008 ; 21(1): 134-141.*

J. Vestbo. Epidemiological studies in mucus secretion. Chapter 1 of "Mucus Hypersecretion in Respiratory Disease". Chichester England: John Wiley and Sons, 2002, pp. 3, 4, and 14-16.*

Hughes JR, Stead LF, Lancaster T. Anxiolytics for smoking cessation (Review). Cochrane Database of Systematic Reviews 2000, Issue 4. Art. No. CD002849, pp. 1-21.*

J. Vestbo, "Epidemiological studies in mucus hypersecretion", in Mucus Hypersecretion in Respiratory Disease. Chichester, West Sussex, England: John Wiley and Sons, 2002, pp. 3, 4, 14-16.*

Nguyen et al. "Complementary anti-inflammatory effects of a B-Blocker and a Corticosteroid in an Asthma Model", Naunyn-Schmiedeberg's Arch Pharmacol (2012) 385:203-210, 8 Pages.

Wise et al. "A Review of Nonpharmacologic and Pharmacologic Therapies for Smoking Cessation" Formulary vol. 43: 44-64 (2008), 12 Pages.

Warner, "Perioperative Abstinence from Cigarettes;physiologic and clinical consequences", Anesthesiology, Anesthesiology, vol. 104, No. 2, Feb. 2006, 12 Pages.

* cited by examiner

USE OF BETA-ADRENERGIC INVERSE AGONISTS FOR SMOKING CESSATION

CROSS-REFERENCES

This application claims priority from U.S. Provisional Patent Application Ser. No. 61/431,308 by R. A. Bond et al., entitled "Use of Beta-Adrenergic Inverse Agonists for Smoking Cessation" and filed Jan. 10, 2011, the contents of which are hereby incorporated herein in their entirety by this reference.

BACKGROUND OF THE INVENTION

The present invention relates to novel methods and compositions employing β-adrenergic inverse agonists for smoking cessation, particularly for controlling or preventing the suite of physical and physiological symptoms that is associated with cessation of smoking: including but not limited to craving, tremor, cough, productive cough and hypersecretion of mucus occurring in individuals attempting to quit smoking, either under the management of a general practitioner or specialist. Specifically, the present invention relates to compositions and methods providing for the chronic administration of selective or non-selective $β_2$-adrenergic inverse agonists as treatments to assist smoking cessation.

The health hazards of tobacco smoking have been well documented. Tobacco-related diseases are some of the biggest killers in the world and are cited as one of the major causes of premature death in most industrialized countries. In the United States, it is estimated that some 500,000 deaths per year are attributable to smoking-related diseases. A recent study has estimated that as much as one-third of the male population of China will have significantly shortened lifespans because of smoking. It has been calculated that male and female smokers lose an average of 13.2 and 14.5 years of life, respectively, because of smoking.

Among the diseases and conditions that have been linked to smoking are lung cancer, heart disease, diseases of the circulatory system such as Buerger's Disease, emphysema, chronic obstructive pulmonary disease, and vascular stenosis. Additionally, smoking is now suspected as a risk factor in Alzheimer's disease and many other diseases.

Additionally, even for non-smokers, smoking causes significant health risks because of second-hand smoke. Additionally, cigarette smoking can be a substantial financial burden on regular smokers; the cost of cigarettes has greatly increased in recent years, in part due to increased taxes.

Many current smokers desire to quit. However, quitting smoking is extremely difficult for many smokers. Smokers may attempt to quit either on their own, using over-the-counter products and techniques, or in a program that includes pharmacotherapy as well as education, support, reinforcement and follow-up. Failure rates, even under the auspices of the best programs are high, for a number of reasons. Nicotine, present in tobacco smoke, is extremely addictive. In low concentrations, nicotine acts as a stimulant and is the main factor contributing to the dependence-forming properties of tobacco smoking. According to the American Heart Association, nicotine addiction is one of the hardest addictions to break, and the pharmacological and behavioral characteristics that determine tobacco addiction are similar to those that determine addiction to illegal drugs of abuse such as cocaine, heroin, and amphetamines.

When a smoker attempts to quit, he or she frequently encounters withdrawal symptoms similar to the withdrawal symptoms encountered by users of illegal drugs of abuse such as cocaine or heroin. These withdrawal symptoms include both physiological and psychological symptoms, including but not limited to craving, tremor, anxiety agitation, exhaustion, cough, and chest pain. Currently approved drugs for smoking cessation include nicotine replacement, to reduce the effects of nicotine replacement, and anxiolytics such as varenicline or buproprion to address the psychological symptoms of smoking cessation. However, no currently approved drugs address the physiological and anatomical changes associated with smoking cessation. As detailed below, one of the significant physical symptoms is mucus hypersecretion and coughing, which can be extremely uncomfortable and annoying to a cigarette smoker attempting to quit smoking.

A number of smoking cessation aids are currently available; however, these smoking cessation aids have high failure rates, may have significant side effects, and, in some cases, do not assist in breaking nicotine addiction. For example, nicotine replacement as monotherapy or in combination has a high failure rate.

Mucus secretion from the epithelium is an important function and occurs in the nose and in the airways. Mucus provides important protective functions such as prevention of drying and capture of foreign particles. Normal airway epithelium function requires mucociliary clearance in which mucus secreted on the surface of the airway epithelium is moved continually up the airways by beating cilia thereby removing any foreign objects. Lack of mucociliary clearance may be caused by a variety of disruptions such as failure of epithelial ciliary beating, lack of ciliated epithelium, minimal to no mucus secretion or hypersecretion of mucus, or a combination of these. Most importantly, the airway epithelium may undergo reversible phenotypical changes to goblet cells that produce and secrete mucus. Hypersecretion of mucus occurs as a consequence of allergies, viral, bacterial or fungal infections, asthma, cystic fibrosis, or COPD. As indicated above, it also occurs in individuals as the result of attempting smoking cessation.

The physical mechanism of coughing serves to expel the mucus from the airway passages (see e.g., "Foundations of Respiratory Care" Pierson and Kacmarek, eds. (1992) Churchill Livingstone Inc. New York, N.Y.; "Harrison's Principles of Internal Medicine", Fauci et al., eds. (1997) 14th Edition, McGraw Hill, New York, N.Y.).

The mucociliary system consists of ciliated epithelial cells, epithelial goblet cells, and serous and mucous cells located in submucosal glands. The cilia are surrounded by an aqueous layer (periciliary fluid) secreted into the lumen of the airway passage by the active transport of chloride and the passive movement of water across the epithelium. The cilia make contact with the mucus floating on this aqueous layer, and via a unidirectional propelling motion provide for movement of mucus toward the glottis (see Pierson and Kacmarek, supra and Fauci et al., supra). Mucus is produced by the epithelial goblet cells and submucosal gland cells and is secreted into the lumen of the airway after degranulation.

Mucus is characterized by the presence of a family of glycoproteins known generally as mucins. Mucins are a family of glycoproteins secreted by the epithelial cells including those at the respiratory, gastrointestinal and female reproductive tracts. Mucins are responsible for the viscoelastic properties of mucus and at least eight mucin genes are known. (D. J. Thornton, et al., J. Biol. Chem. 272, 9561-9566 (1997)). Analysis of airway secretions has identified MUC5AC and MUC5B as the primary mucin constituents of the respiratory mucus gel.

While mucus generally facilitates the clearance of inhaled particles or infectious agents, hypersecretion of mucus in the airways may cause progressive airway obstruction. In peripheral airways, cough is ineffective for clearing secretions. Furthermore, because of their small dimensions, small airways containing many goblet cells are especially vulnerable to airway plugging by mucus. Airway hypersecretion affects a substantial number of individuals; it is seen in a variety of pulmonary diseases, such as chronic bronchitis, acute asthma, cystic fibrosis, and bronchiectasis. Also, other conditions such as pulmonary fibrosis and tuberculosis are also characterized by mucus hypersecretion. As indicated above, mucous hypersecretion is a significant symptom in cigarette smokers and smokers attempting smoking cessation, and is frequently responsible for failure of the attempt to cease smoking. Cigarette smoking causes the majority of cases of lung cancer and chronic obstructive pulmonary disease, which consists of chronic bronchitis and emphysema. The definition of chronic bronchitis (reference ATS) reflects mucus hypersecretion for at least 2 months for consecutive years.

Hypersecretion has also been implicated in cystic fibrosis, which is one of the most common fatal genetic diseases in the world. Cystic fibrosis is an autosomal recessive disease that causes the airway mucosal cell to become unresponsive to cyclic-AMP-dependent protein kinase activation of the membrane chloride ion channels (Pierson and Kacmarek, supra and Fauci, et al., supra). The subsequent electrolyte imbalance reduces the level of hydration of the airway mucus, thus resulting in highly viscous mucus in the lungs of an individual afflicted with cystic fibrosis. Hypersecretion obstructs the air passages of individuals with cystic fibrosis, further compromising lung function.

Classical modalities of treating individuals afflicted with chronmic cough and mucus hypersecretion include antibiotic therapy, bronchodilators, use of systemic or inhaled corticosteroids, liquefaction of the mucus by oral administration of expectorants, e.g. guaifenesin (sold under a variety of trade names such as Organidin® or Iophen™) or iodinated glycerol (also sold under a variety of trade names such as Par Glycerol™ or R-Gen™, and aerosol delivery of "mucolytic" agents, such as water or hypertonic saline solution. Cough suppressants include narcotic products such as codeine. Therapy for cystic fibrosis is the administration of DNAse to target the DNA-rich mucus or sputum (Shak, et al (1990) Proc. Nat. Acad. (USA) 87:9188-9192; Hubbard, R. C. et al. (1991) N. Engl. J. Med. 326:812). Other drugs that are used are acetylcysteine (sold under the trade name of Mucomyst™, Mucosil-10™, Mucosil-20™ and others). In addition, chest physical therapy consisting of percussion, vibration and drainage are also used to facilitate clearance of viscous mucus. Specifically, there is a need for a specific modality that will reduce the formation of mucus secretions in the airways, by enabling or causing the reversal of mucus (goblet) cells to ciliated epithelium.

Additionally, antihistamines and decongestants are sometimes used in an attempt to achieve symptomatic relief from respiratory conditions characterized by the presence of excess mucus secretion. Antihistamines, which dry the respiratory tract, have little or no value in treating a cough, except when it is caused by an upper respiratory allergy. With coughs from other causes, such as bronchitis, the drying actions of antihistamines can be harmful, thickening respiratory secretions and making them more difficult to remove.

Currently a number of pharmaceutical substances are indicated for or have been shown to be useful in treating the symptoms of COPD, including salmeterol xinafoate, fluticasone propionate, ipratropium bromide, (2R,3R,4S,5R)-2-[6 amino-2-(1S-hydroxymethyl-2-phenyl-ethylamino)-purin-9-yl]-5-(2-ethyl-2H-tetrazol-5-yl)-tetrahydrofuran-3,4-diol tiotropiurn, 4-hydroxy-7-[2-[[2-[[3-(2-phenylethyoxy)propyl]sulfonyl]ethyl]amino]ethyl-2-(3H)-benzothiazolone and cis-20,4-cyano-4-[3-(cyclopentyloxy)-4-methoxyphenyl]cyclohexanecarboxylic acid. However, there remains a need for the development of specific agents that can reverse mucus hypersecretion and can prevent the transformation of epithelial cells of the respiratory system into goblet cells or reverse goblet cell phenotype to ciliated columnar epithelium. There is a particular need for such agents that can block mucus hypersecretion in individuals experiencing mucus hypersecretion as the result of chronic cough.

More efficient and long-lasting therapeutic modalities that can reverse the anatomical, histological, and physiological changes leading to symptoms that are a consequence of smoking cessation such as tremor, craving, mucus hypersecretion and chronic unproductive or productive cough can bring about the recovery of normal mucociliary clearance in diseased nasal and/or pulmonary airways are needed. Most particularly, there is a need for efficient therapeutic modalities that can treat or block one or more of the suite of symptoms in patients attempting smoking cessation in order to reduce the physical symptoms associated with nicotine withdrawal and increase the effectiveness of smoking cessation programs.

SUMMARY OF THE INVENTION

Methods and compositions according to the present invention provide an efficient means of preventing or reducing the anatomical or physiological changes that cause symptoms associated with smoking cessation including but not limited to tremor, craving, mucus hypersecretion and acute or chronic cough by the regular (chronic) administration of β-adrenergic inverse agonists. These methods and compositions are of particular efficacy in blocking or treating the suite of symptoms that accompanies attempts at smoking cessation. These symptoms include tremor, cough, and mucus hypersecretion.

One aspect of the invention is a method of preventing or controlling mucus hypersecretion in the respiratory tract comprising administering a therapeutically effective quantity of a β-adrenergic inverse agonist to a subject with mucus hypersecretion or at risk of mucus hypersecretion, particularly to a subject attempting smoking cessation or who is about to cease smoking. The method can be initiated before the subject has actually attempted to cease smoking.

Typically, the β-adrenergic inverse agonist is selected from the group consisting of $β_2$-selective inverse agonists, and non-selective inverse agonists having inverse agonist activity against both $β_1$- and $β_2$-adrenergic receptors. Preferably, the β-adrenergic inverse agonist is a $β_2$-selective inverse agonist.

Typically, the β-adrenergic inverse agonist is selected from the group consisting of nadolol, bupranolol, butoxamine, carazolol, carvedilol, ICI-118,551, levobunolol, metoprolol, propranolol, sotalol, and timolol, and the salts, solvates, analogues, congeners, mimetics, bioisosteres, stereoisomers, hydrolysis products, metabolites, precursors, and prodrugs thereof.

In one preferred alternative, the β-adrenergic inverse agonist is selected from the group consisting of nadolol and a compound of formula (I)

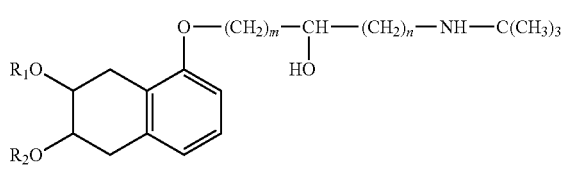

(I)

wherein $R_1$ is hydrogen or lower alkyl, $R_2$ is hydrogen or lower alkyl, and m and n are 1 to 3, with the proviso that where $R_1$ and $R_2$ are both hydrogen and m is 1, n is other than 1. More preferably, in this alternative, the β-adrenergic inverse agonist is nadolol.

In another preferred alternative, the β-adrenergic inverse agonist is selected from the group consisting of carvedilol and analogues of carvedilol of formula (II) wherein $R_1$ is hydrogen or lower alkyl, $R_2$ is hydrogen or lower alkyl, and $R_3$ is hydrogen or lower alkyl, with the proviso that all of $R_1$, $R_2$, and $R_3$ are not all hydrogen. More preferably, in this alternative, the β-adrenergic inverse agonist is carvedilol.

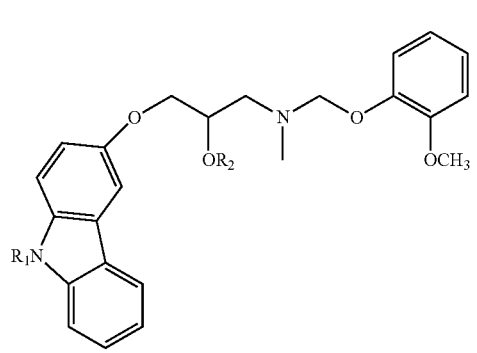

(II)

In still another preferred alternative, the β-adrenergic inverse agonist is selected from the group consisting of timolol and analogues of timolol of formula (III) wherein $R_1$ is hydrogen or lower alkyl and $R_2$ is hydrogen or lower alkyl, with the proviso that both $R_1$ and $R_2$ are not hydrogen. More preferably, in this alternative, the β-adrenergic inverse agonist is timolol.

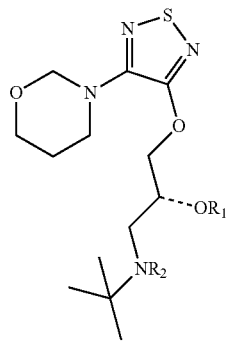

(III)

In still another preferred alternative, the β-adrenergic inverse agonist is selected from the group consisting of metoprolol and analogues of metoprolol of formula (IV) wherein $R_1$ is hydrogen or lower alkyl and $R_2$ is hydrogen or lower alkyl, with the proviso that both $R_1$ and $R_2$ are not hydrogen. More preferably, in this alternative, the β-adrenergic inverse agonist is metoprolol.

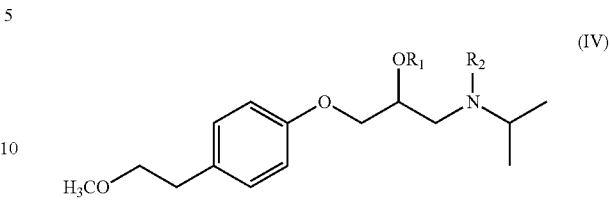

(IV)

In still another preferred alternative, the β-adrenergic inverse agonist is selected from the group consisting of ICI-118,551 and analogues of ICI-118,551 of formula (V) wherein $R_1$ is lower alkyl, $R_2$ is hydrogen or lower alkyl, $R_3$ is hydrogen or lower alkyl, $R_4$ is hydrogen or lower alkyl, $R_5$ is lower alkyl, and $R_6$ is lower alkyl, with the proviso that all of $R_1$, $R_3$, $R_5$, and $R_6$ are not methyl and all of $R_2$ and $R_4$ are not hydrogen. More preferably, in this alternative, the β-adrenergic inverse agonist is ICI-118,551.

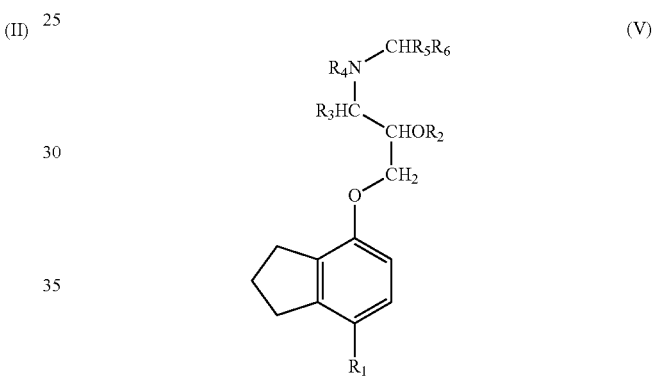

(V)

Typically, the method results in continuous levels of the β-adrenergic inverse agonist in the bloodstream of the subject. Typically, the method exerts a therapeutic effect that is an upregulation of pulmonary β-adrenergic receptors. Typically, the method inhibits or reverses the conversion of epithelialiated airways into airways dominated by mucus-producing goblet cells.

Various routes of administration are known in the art. In particular, the β-adrenergic inverse agonist can be administered via a transdermal patch or by chewing gum.

Another aspect of the present invention is a method of treating or preventing a disease or condition characterized by mucus hypersecretion comprising administering a therapeutically effective quantity of a β-adrenergic inverse agonist to a subject with such a disease or condition or at risk of contracting such a disease or condition. The inverse agonists suitable for this method are those described above. In one preferred alternative, the disease or condition is nicotine withdrawal.

Yet another aspect of the present invention is a method of preventing or controlling mucus hypersecretion in the respiratory tract comprising administering to a subject with mucus hypersecretion or at risk of mucus hypersecretion:

(1) a therapeutically effective quantity of a β-adrenergic inverse agonist; and (2) a therapeutically effective quantity of an additional compound to treat mucus hypersecretion.

As described above, the mucus hypersecretion can be associated with smoking cessation and the subject is attempting smoking cessation or is about to cease smoking. The method can be applied to a subject who is actually attempting smoking cessation or can be applied prophylactically to a subject who is about to cease smoking.

The inverse agonists suitable for this method are those described above. The additional compound to treat mucus hypersecretion can be, but is not limited to: (1) an antibiotic; (2) a DNase; (3) a bronchodilator; (4) a corticosteroid; (5) an epidermal growth factor antagonist; (6) an expectorant; (7) (2R,3R,4S,5R)-2-[6 amino-2-(1S-hydroxymethyl-2-phenylethylamino)-purin-9-yl]-5-(2-ethyl-2H-tetrazol-5-yl)-tetrahydrofuran-3,4-diol; (8) 4-hydroxy-7-[2-[[2-[[3-(2-phenylethoxy)propyl]sulfonyl]ethyl]amino]ethyl-2-(3H)-benzothiazolone; (9) cis-20,4-cyano-4-[3-(cyclopentyloxy)-4-methoxyphenyl]cyclohexanecarboxylic acid; or (10) a PDE4 inhibitor.

Yet another aspect of the present invention is a method of preventing or controlling mucus hypersecretion in the respiratory tract in a subject attempting smoking cessation who is at risk for mucus hypersecretion comprising administering to the subject:

(1) a therapeutically effective quantity of a β-adrenergic inverse agonist; and (2) a therapeutically effective quantity of an additional compound to promote smoking cessation.

The inverse agonists suitable for this method are those described above. The additional compound to promote smoking cessation can be, but is not limited to, selected from the group consisting of buproprion, varenicline, clonidine, and nortriptyline, and the salts, solvates, analogues, congeners, mimetics, bioisosteres, stereoisomers, hydrolysis products, metabolites, precursors, and prodrugs thereof.

Yet another aspect of the present invention is a method of preventing or controlling mucus hypersecretion in the respiratory tract in a subject attempting smoking cessation who is at risk for mucus hypersecretion comprising administering to the subject:

(1) a therapeutically effective quantity of a β-adrenergic inverse agonist;

(2) a therapeutically effective quantity of an additional compound to treat mucus hypersecretion; and (3) a therapeutically effective quantity of an additional compound to promote smoking cessation.

In this method, the β-adrenergic inverse agonist, the additional compound to treat mucus hypersecretion, and the additional compound to promote smoking cessation are as described above.

Another aspect of the present invention is a pharmaceutical composition comprising:

(1) a therapeutically effective quantity of a β-adrenergic inverse agonist as described above; and (2) at least one pharmaceutically acceptable carrier.

Another aspect of the present invention is a pharmaceutical composition comprising:

(1) a therapeutically effective quantity of a β-adrenergic inverse agonist as described above;

(2) a therapeutically effective quantity of an additional compound to treat mucus hypersecretion as described above; and (3) at least one pharmaceutically acceptable carrier.

Yet another aspect of the invention is a pharmaceutical composition comprising:

(1) a therapeutically effective quantity of a β-adrenergic inverse agonist as described above;

(2) a therapeutically effective quantity of an additional compound to promote smoking cessation as described above; and (3) at least one pharmaceutically acceptable carrier.

Still another aspect of the invention is a pharmaceutical composition comprising:

(1) a therapeutically effective quantity of a β-adrenergic inverse agonist as described above;

(2) a therapeutically effective quantity of an additional compound to promote smoking cessation;

(3) a therapeutically effective quantity of an additional compound to treat mucus hypersecretion as described above; and (4) at least one pharmaceutically acceptable carrier.

Pharmaceutical compositions according to the present invention can be formulated for administration via a transdermal patch or as chewing gum.

BRIEF DESCRIPTION OF THE DRAWINGS

The following invention will become better understood with reference to the specification, appended claims, and accompanying drawings, where:

DETAILED DESCRIPTION OF THE INVENTION

Figure 1:
FIG. 1 is a photomicrograph of a section from lung tissue of control mice showing normal epithelium; staining is with hematoxylin-eosin.
Figure 1:

As used herein, in the generally accepted two-state model of receptor theory, the term "agonist" is defined as a substance that has an affinity for the active site of a receptor and thereby preferentially stabilizes the active state of the receptor, or a substance, including, but not limited to, drugs, hormones, or neurotransmitters, that produces activation of receptors and enhances signaling by those receptors. Irrespective of the mechanism or mechanisms of action, an agonist produces activation of receptors and enhances signaling by those receptors.

As used herein, in the two-state model of receptor theory, the term "antagonist" is defined as a substance that does not preferentially stabilize either form of the receptor, active or inactive, or a substance, including, but not limited to, drugs, hormones, and neurotransmitters, that prevents or hinders the effects of agonists and/or inverse agonists. Irrespective of the mechanism or mechanisms of action, an antagonist prevents or hinders the effects of agonists and/or inverse agonists.

As used herein, in the two-state model of receptor theory, the term "inverse agonist" is defined as a substance that has an affinity for the inactive state of a receptor and thereby preferentially stabilizes the inactive state of the receptor, or a substance, including, but not limited to, drugs, hormones, or neurotransmitters, that produces inactivation of receptors and/or prevents or hinders activation by agonists, thereby reducing signaling from those receptors.

As used herein, the term "concurrent administration" refers to the administration of two or more active agents sufficiently close in time to achieve a combined therapeutic effect that is preferably greater than that which would be achieved by the administration of either agent alone. Such concurrent administration can be carried out simultaneously, e.g., by administering the active agents together in a common pharmaceutically acceptable carrier in one or more doses.

The term "subject," as used herein, refers to human or animal species. In general, methods and compositions according to the present invention can be used to treat not only humans, but also socially or economically important animal species such as cows, horses, sheep, pigs, goats, dogs, and cats. Unless specified, methods and compositions according to the present invention are not limited to treatment of humans. However, inasmuch as only humans are known to smoke tobacco, methods and compositions directed to the cessation of smoking are considered herein to be directed to the treatment of humans.

The term "therapeutically effective amount," as used herein, refers to an amount of a therapeutic agent or composition effective to treat, ameliorate, or prevent a desired disease or condition, or to exhibit a detectable therapeutic or preventative effect. The effect can be detected by, for example, chemical markers, antigen levels, or changes in physiological indicators such as airway resistance, forced expiratory volume after 1 second ($FEV_1$), the concentration of the challenge agent methacholine causing a 20% decrease in $FEV_1$ ($PC_{20}$), or other indicators, such as, but not limited to: (1) prebronchodilator $FEV_1$ (forced expiratory volume over 1 second); (2) postbronchodilator $FEV_1$ (forced expiratory volume over 1 second after inhalation of albuterol rescue medication); (3) FVC (forced vital capacity); (4) FEF25-75% (flow during 25-75% of vital capacity); (5) PEFR (peak expiratory flow rate); (6) TLC (total lung capacity); (7) VC (vital capacity); (8) FRC (volume in lungs after normal exhalation); (9) exhaled nitrous oxide; (10) eosinophil levels in lung and/or blood; or (11) IgE levels. Therapeutic effects also include reduction in physical symptoms, such as decreased bronchoconstriction or decreased airway resistance, and can include subjective improvements in well-being noted by the subjects or their caregivers. Other tests can include the following: rescue medication use per day or other time period; asthma exacerbations over a defined time period, e.g. year (an exacerbation is unscheduled trip to doctor, ER visit, hospitalization); alteration in inhaled/oral steroid dose level; Juniper asthma control questionnaire symptom score (ACQ); Asthma Symptom Score (singly or all combined; nocturnal awakening due to wheeze/cough, daytime wheeze, daytime cough, shortness of breath, chest tightness, expectoration of mucus or sputum). The precise therapeutically effective amount for a subject will depend upon the subject's size, weight, and health, the nature and extent of the condition affecting the subject, and the therapeutics or combination of therapeutics selected for administration, as well as variables such as liver and kidney function that affect the pharmacokinetics of administered therapeutics. Thus, it is not useful to specify an exact effective amount in advance. However, the effective amount for a given situation can be determined by routine experimentation and is within the judgment of the clinician. In the case of the use of inverse agonists to treat or prevent mucus hypersecretion in subjects attempting to cease smoking, the term "therapeutically effective amount" can be defined in terms of the subjective discomfort and nicotine withdrawal symptoms experienced by the subject, a decrease in the volume of mucus secretion associated with nicotine withdrawal symptoms, an improved mood and psychological outlook exhibited by the subject, or the ability of the subject to refrain from returning to cigarette smoking. Other parameters suitable for determining a therapeutically effective amount of inverse agonists or other therapeutic agents in the case of subjects attempting to cease smoking are known in the art.

One embodiment of the present invention is a method of preventing or controlling mucus hypersecretion in the respiratory tract comprising administering a therapeutically effective quantity of a β-adrenergic inverse agonist to a subject with mucus hypersecretion or at risk of mucus hypersecretion. The subject with chronic cough and/or mucus hypersecretion or at risk of mucus hypersecretion is typically a subject who is attempting to quit smoking or who is about to do so.

Similarly, another embodiment of the present invention is a method of treating or preventing a disease or condition characterized by mucus hypersecretion comprising administering a therapeutically effective quantity of a β-adrenergic inverse agonist to a subject with such a disease or condition or at risk of contracting such a disease or condition. As detailed above, the subject can be a subject who is attempting to quit smoking or is planning to do so.

In classical receptor theory, two classes of G protein-coupled receptor (GPCR) ligands were considered: agonist and antagonist. Receptors were believed to exist in a single quiescent state that could only induce cellular signaling upon agonist binding to produce an activated receptor state. In this model, binding by antagonists produced no cellular signaling but simply prevented receptors from being bound and activated by agonists. Then, Costa and Herz demonstrated that receptors could be manipulated into a constitutive or spontaneously active state that produced cellular signaling in the absence of agonist occupation. They also provided evidence that certain compounds inactivate those spontaneously active receptors (T. Costa & A. Herz, "Antagonists with Negative Intrinsic Activity at δ Opioid Receptors Coupled to GTP-Binding Proteins," *Proc. Natl. Acad. Sci. USA* 86: 7321-7325 (1989)). There is further evidence that GPCRs exist in constitutively or spontaneously active states that are inactivated to some degree by inverse agonists (R. A. de Ligt et al., "Inverse Agonism at G Protein-Coupled Receptors: (Patho)physiological Relevance and Implications for Drug Discovery," *Br. J. Pharmacol.* 130:1-12 (2000); G. Milligan et al., "Inverse Agonism: Pharmacological Curiosity or Potential Therapeutic Strategy?," *Trends Pharmacol. Sci.* 16: 10-13 (2000)).

The basis of the strategy of this embodiment of the invention is the recognition of the existence of inverse agonists and the understanding of the effect that chronic treatment with inverse agonists has on receptor function. What is an inverse agonist and how does it function? Receptors, such as β-adrenergic receptors that respond to adrenalin (epinephrine), typically exist in an equilibrium between two states, an active state and an inactive state. When receptors bind to agonists, such as adrenalin for the β-adrenoceptors, they stop them from cycling back into the inactive state, thus shifting the equilibrium between the active and inactive states according to the Law of Mass Action. This occurs because those receptors bound to agonists are removed from the equilibrium. Typically, antagonists bind to the receptors, but prevent the binding of agonists. However, molecules known as "inverse agonists" bind to the receptors in the inactive state, causing the equilibrium between the active and the inactive state to shift toward the inactive state. This is not merely a matter of blocking agonist binding.

Moreover, there is a population of spontaneously active receptors in vivo. These receptors provide a baseline constitutive level of activity; the activity is never entirely "off."

As indicated above, it has been well demonstrated that chronic administration of β-adrenergic agonists causes agonist-dependent desensitization. Upon acute administration of β-agonists, adrenergic receptors are internalized, thereby preventing them from being restimulated further for pulmonary relaxation. With chronic administration of β-agonists, there is actually a downregulation in the total number of β-adrenergic receptors. The consequence may be the observed loss of responsiveness seen in asthmatic patients on long-acting β-agonists, and referred to as tolerance or tachyphylaxis, as described above.

The treatment methods of the present invention are based on the discovery that a chronic administration of an inverse agonist has the effect of upregulating the population of active β-adrenergic receptors. The observed activity may be due to the receptor's constitutive baseline activity or the combined effect of increased level of receptors responding to endogenous agonists. This leads to the seemingly paradoxical result that the administration of a drug that would appear, at first blush, to degrade a physiological function, such as by causing airway hyperresponsiveness in asthma, can, if administered chronically, enhances that physiological function by up-regulating the population of spontaneously active β-adrenergic receptors associated with that physiological function. Additionally or alternatively, the inverse agonist may also improve coupling of the receptor to its cognate internal G protein thereby resulting in a higher output of result such as the production of cellular cAMP with a smaller proportion of activated receptors. This is a specific application of the principle of "paradoxical pharmacology."

In U.S. Pat. No. 5,116,867 to Klein et al., incorporated herein by this reference, D-propranolol or racemic mixtures composed of 85% or more of the D form was proposed for the treatment of asthma. The D-form of propranolol was 1/100 as potent as the L-form in inhibiting the β-adrenergic receptor. In contrast, this patent specifies the use of the active form or of racemic mixtures containing 50% or more of the active β-adrenergic antagonist.

In U.S. Pat. No. 6,284,800 to Broder et al., incorporated herein by this reference, the D forms of propranolol, metoprolol, carvedilol, or bisoprolol were proposed for the treatment of asthma. Experiments were performed comparing the D-form versus the L-form of propranolol, demonstrating that acute administration of D-propranolol was beneficial in inhibiting antigen-induced bronchoconstriction and reducing airway hyperresponsiveness. In contrast, acute administration of the L-form increased specific lung resistance as expected for an active β-adrenergic agonist. The D form of propranolol was inactive with respect to β-adrenergic receptors. Consequently, U.S. Pat. No. 6,284,800 does not deal with inverse agonism.

PCT Patent Publication No. WO 02/29534, by Bond, had proposed compounds with $\beta_1$ and/or $\beta_2$ antagonist activity that inhibited β-adrenergic receptors to treat allergic and inflammatory disorders including asthma and chronic obstructive pulmonary disease. Experiments were performed in which asthmatic mice were chronically treated with compounds characterized as β-antagonists, including alprenolol, carvedilol, and ICI-118,551. Then, tracheas from the mice were excised and contraction of the tracheas in response to methacholine was monitored as a surrogate for an asthma attack. The most effective compound was alprenolol, followed by carvedilol, then ICI-118,551.

More physiologically relevant experiments in a mouse model of obstructive lung disease performed by the inventor in the present application have demonstrated that alprenolol, originally thought to be beneficial chronically, does not reduce airway hyperresponsiveness compared to untreated sensitized and challenged mice. Even though alprenolol is a β-adrenergic antagonist, it has partial agonist activity. Carvedilol is a $\beta_1/\beta_2$ non-selective adrenergic antagonist with $\alpha_1$-adrenergic antagonist activity. In the experiments reported in the present application, chronic administration of carvedilol does reduce airway hyperresponsiveness, which would be beneficial to patients with asthma, but it also shifts the sensitivity of the responsiveness to methacholine to lower concentrations, which could be detrimental to asthmatics.

Moreover, in the experiments reported in PCT Patent Publication No. WO 02/29534, tracheas were excised from mice, leaving behind the vast majority of the pulmonary airways. In mice, the trachea contains almost exclusively only $\beta_1$ adrenergic receptors whereas the remainder of the airways is a mixture of $\beta_1$ and $\beta_2$ adrenergic receptors. In contrast, human airways, both the trachea and the smaller airways, contain almost exclusively $\beta_2$ receptors. Consequently, the experiments reported in PCT Patent Publication No. WO 02/29534 have little predictive value for human asthma. The experiments reported in the present application more closely reflect human physiology.

β-adrenergic antagonist drugs or "beta blockers" are treated as having the same activity in conventional pharmacology. Beta blockers are further classified based on their selectivity or lack thereof for either the $\beta_1$ (termed "cardioselective") or $\beta_1/\beta_2$ ("nonselective") or $\beta_2$ selective only. Additionally, beta blockers can be classified as to whether or not they have partial agonist activity or are actually inverse agonists. The latter definition is based on the new appreciation, recited in the present application, that many G-coupled protein receptors, including the β-adrenergic receptors, exhibit low level spontaneous activity that can be further prevented by the binding of the inverse agonists to the receptor. This distinction was not made in PCT Patent Publication No. WO 02/29534, which referred simply to "antagonists."

Despite this knowledge of the subclasses of beta blockers in the field, many scientists have continued to treat compounds from the different subclasses as one class. An example of this is the clinical testing in 1998-1999 of the beta blocker bucindolol for congestive heart failure. Previously, two other beta blockers, metoprolol and carvedilol, had been clinically tested and demonstrated significant mortality reduction in patients with CHF. Bucindolol failed to demonstrate any benefit over placebo, and thus clinical testing was discontinued. The inventor of the present application notes that both metoprolol and carvedilol are β-inverse agonists whereas bucindolol is a neutral antagonist with partial agonist activity. Consequently, the inventor of the present application would predict that only β-adrenergic inverse agonists would be effective in treatment of CHF. In the same vein, the inventor of the present application predicts that only β-adrenergic inverse agonists will be effective for chronic treatment of asthma airway hyperresponsiveness. This distinction is not made or suggested in PCT Patent Publication No. WO 02/29534. This prediction is borne out in the present invention by the refutation that the beta blocker alprenolol, a partial agonist, previously thought to be the preferred drug in a flawed murine asthma model, was found to be without any activity in the present invention.

Instead, this invention provides for the use of the active β-adrenergic receptor binding forms of β-adrenergic inverse agonists in the prevention or suppression of mucus hypersecretion, leading to a new modality for assisting smoking cessation. This modality treats the physiological effects of smoking cessation, such as tremor, cough, and mucus hypersecretion, in contrast to other smoking cessation methods, which are primarily directed to the psychological or behavioral aspects. The inverse agonists can be in pure or substantially pure enantiomeric or diastereomeric form or can be racemic mixtures. In many cases, the active form of such compounds is the L form when there is only one chiral center. In the case of nadolol, which has three chiral centers and potentially 12 isomers, though, typically, only two are formed during synthesis, the most active form is the RSR form of nadolol.

Especially preferred for use according to the invention are the β-adrenergic inverse agonists: nadolol, e.g., as the hydrochloride: bupranolol, e.g., as the hydrochloride; butoxamine, e.g., as the hydrochloride; carazolol, e.g., as the hydrochloride; carvedilol, e.g., as the hydrochloride; ICI-118,551, i.e., as the hydrochloride; levobunolol, e.g., as the hydrochloride; metoprolol, as the tartrate or succinate; propranolol, e.g., as the hydrochloride; sotalol, e.g., as the hydrochloride; timolol; e.g., as the hydrochloride; and the salts, solvates, analogues, congeners, mimetics, bioisosteres, stereoisomers, hydrolysis products, metabolites, precursors, and prodrugs thereof. Particularly preferred inverse agonists are carvedilol, nadolol, and ICI-118,551. Most particularly preferred inverse agonists are nadolol and ICI-118,551. As used herein, the recitation of an inverse agonist compound, or, where appropriate, an agonist compound, includes all pharmaceutically acceptable salts of that inverse agonist compound or agonist compound unless excluded. Thus, the recitation of nadolol or ICI-118,551 as the hydrochloride does not exclude other pharmaceutically acceptable salts that have been prepared or that can be prepared.

The inverse agonists useful in methods and compositions according to the invention typically display inverse agonism to $β_2$-adrenergic receptors; either as non-selective inverse agonists that display inverse agonism to both the $β_1$- and $β_2$-adrenergic receptors or as a selective $β_2$-inverse agonist.

Preferably, inverse agonists useful in methods and compositions according to the invention both reduce airway hyperresponsiveness and, when tested in the asthmatic mouse model, do not shift the methacholine response to the left (i.e., to lower methacholine concentrations).

Specifically, also expected to be within the scope of the invention are analogues of nadolol of formula (I) wherein $R_1$ is hydrogen or lower alkyl, $R_2$ is hydrogen or lower alkyl, and m and n are 1 to 3, with the proviso that where $R_1$ and $R_2$ are both hydrogen and m is 1, n is other than 1. As used herein, the term "lower alkyl" is defined as a straight or branched hydrocarbyl residue of 1-6 carbon atoms.

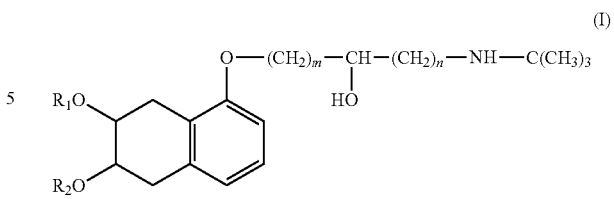

Also specifically expected to be within the scope of the invention are analogues of carvedilol of formula (II) wherein $R_1$ is hydrogen or lower alkyl, $R_2$ is hydrogen or lower alkyl, and $R_3$ is hydrogen or lower alkyl, with the proviso that all of $R_1$, $R_2$, and $R_3$ are not all hydrogen.

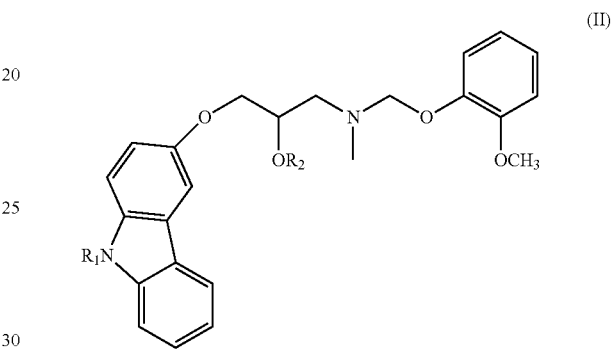

Also expected to be within the scope of the invention are analogues of timolol of formula (III) wherein $R_1$ is hydrogen or lower alkyl and $R_2$ is hydrogen or lower alkyl, with the proviso that both $R_1$ and $R_2$ are not hydrogen.

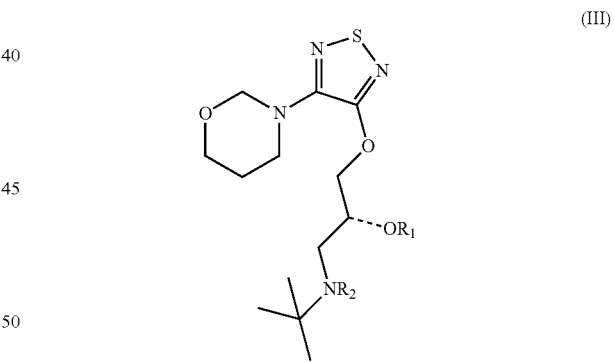

Further expected to be within the scope of the invention are analogues of metoprolol of formula (IV) wherein $R_1$ is hydrogen or lower alkyl and $R_2$ is hydrogen or lower alkyl, with the proviso that both $R_1$ and $R_2$ are not hydrogen.

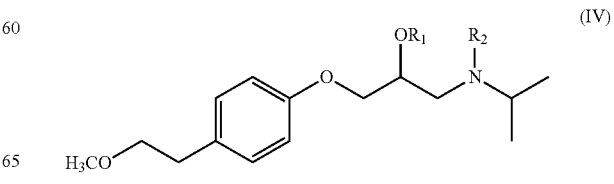

Also further expected to be within the scope of the invention are analogues of ICI-118,551 of formula (V) wherein $R_1$ is lower alkyl, $R_2$ is hydrogen or lower alkyl, $R_3$ is hydrogen or lower alkyl, $R_4$ is hydrogen or lower alkyl, $R_5$ is lower alkyl, and $R_6$ is lower alkyl, with the proviso that all of $R_1$, $R_3$, $R_5$, and $R_6$ are not methyl and all of $R_2$ and $R_4$ are not hydrogen.

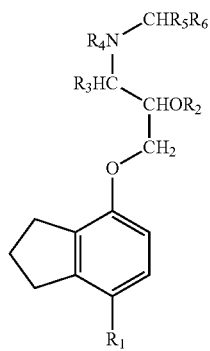

(V)

In the case of salts, it is well known that organic compounds, including compounds having activities suitable for methods according to the present invention, have multiple groups that can accept or donate protons, depending upon the pH of the solution in which they are present. These groups include carboxyl groups, hydroxyl groups, amino groups, sulfonic acid groups, and other groups known to be involved in acid-base reactions. The recitation of a compound or analogue includes such salt forms as occur at physiological pH or at the pH of a pharmaceutical composition unless specifically excluded. Pharmacologically acceptable salts include, but are not limited to, the salts described below.

Similarly, prodrug esters can be formed by reaction of either a carboxyl or a hydroxyl group on compounds or analogues suitable for methods according to the present invention with either an acid or an alcohol to form an ester. Typically, the acid or alcohol includes a lower alkyl group such as methyl, ethyl, propyl, isopropyl, butyl, isobutyl, and tertiary butyl. These groups can be substituted with substituents such as hydroxy, or other substituents. Such prodrugs are well known in the art and need not be described further here. The prodrug is converted into the active compound by hydrolysis of the ester linkage, typically by intracellular enzymes. Other suitable groups that can be used to form prodrug esters are well known in the art. For example prodrugs can include amides prepared by reaction of the parent acid compound with a suitable amine. In some cases it is desirable to prepare double ester type prodrugs such as (acyloxy) alkyl esters or ((alkoxycarbonyl)oxy)alkyl esters. Suitable esters as prodrugs include, but are not necessarily limited to, methyl, ethyl, propyl, isopropyl, n-butyl, isobutyl, tert-butyl, morpholinoethyl, and N,N-diethylglycolamido. Methyl ester prodrugs may be prepared by reaction of the acid form of a compound having a suitable carboxylic acid group in a medium such as methanol with an acid or base esterification catalyst (e.g., NaOH, $H_2SO_4$). Ethyl ester prodrugs are prepared in similar fashion using ethanol in place of methanol. Morpholinylethyl ester prodrugs may be prepared by reaction of the sodium salt of a suitable compound (in a medium such as dimethylformamide) with 4-(2-chloroethyl)morphine hydrochloride (available from Aldrich Chemical Co., Milwaukee, Wis. USA.

Pharmaceutically acceptable salts include inorganic or organic acid salts such as hydrochloride, hydrobromide, hydroiodide, sulfate, phosphate, fumarate, maleate, acetate, citrate, lactate, tartrate, sulfamate, malonate, succinate, methanesulfonate, ethanesulfonate, benzenesulfonate, p-toluenesulfonate, cyclohexylsulfamate, quinate, formate, cinnamate, picrate, propionate, succinate, glycolate, gluconate, ascorbate, benzoate, anthranilate, mesylate, p-hydroxybenzoate, phenylacetate, mandelate, embonate, pantothenate, 2-hydroxyethanesulfonate, sulfanilate, stearate, cyclohexylaminosulfonate, algenate, β-hydroxybutyrate, salicylate, galactarate, galacturonate, and other suitable salts. Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid, as well as the other corresponding acids listed above.

Pharmaceutically acceptable salts also include salts with bases such as alkali metal salts such as sodium or potassium, as well as pyridine salts, ammonium salts, piperazine salts, diethylamine salts, nicotinamide salts, calcium salts, magnesium salts, zinc salts, lithium salts, methylamino salts, triethylamino salts, dimethylamino salts, N,N'-dibenzylethylenediamino salts, choline salts, diethanolamine salts, chloroprocaine salts, ethylenediamino salts, meglumine salts, procaine salts, and tris(hydroxymethyl) aminomethane salts. Such salts can be derived using the appropriate base.

The subject to be treated can be a human patient or a socially or economically important animal, including, but not limited to, a dog, a cat, a horse, a cow, a sheep, a goat, or a pig. Methods according to the present invention are not limited to the treatment of humans. However, inasmuch as only humans are known to smoke tobacco, methods and compositions directed to the cessation of smoking are considered herein to be directed to the treatment of humans.

Typically, methods of administration of β-adrenergic inverse agonists according to the present invention address one or more of the physiological symptoms associated with smoking cessation, including, but not limited to, tremor, mucus hypersecretion, and cough. This activity provides a unique approach to smoking cessation and complements other methods that treat psychological and behavioral issues.

Typically, the method of administration of the β-adrenergic inverse agonist results in continuous levels of the β-adrenergic inverse agonist in the bloodstream of the subject. Typically, the method exerts a therapeutic effect that is an upregulation of pulmonary β-adrenergic receptors. Typically, the method exerts a therapeutic effect that is increased pulmonary airway relaxation responsiveness to $β_2$-adrenergic agonist drugs. This provides for combination therapy, discussed in detail below.

Typically, methods according to the present invention inhibit or reverse the transformation of epithelial cells of the respiratory tract into mucus-producing goblet cells.

The β-adrenergic inverse agonist can be administered in conjunction with one or more pharmaceutical excipients. The pharmaceutical excipients can include, but are not necessarily limited to, calcium carbonate, calcium phosphate, various sugars or types of starch, cellulose derivatives, gelatin, vegetable oils, polyethylene glycols and physiologically compatible solvents. Other pharmaceutical excipients are well known in the art. The β-adrenergic inverse agonist can be administered in conjunction with one or more pharmaceutically acceptable carriers. Exemplary pharmaceutically acceptable carriers include, but are not limited to, any and/or all of solvents, including aqueous and non-aqueous solvents, dispersion media, coatings, antibacterial and/or antifungal agents, isotonic and/or absorption delaying agent, and/or the like. The use of such media and/or agents for pharmaceutically active substances is well known in the art. Except insofar as any conventional medium, carrier, or agent is incompatible with the active ingredient or ingredients, its use in a composition according to the present invention is contemplated. Supplementary active ingredients can also be incorporated into the compositions, especially as described below under combination therapy. For administration of any of the compounds used in the present invention, preparations should meet sterility, pyrogenicity, general safety, and purity standards as required by the FDA Office of Biologics Standards or by other regulatory organizations regulating drugs.

Thus, the β-adrenergic inverse agonist can be formulated for oral, sustained-release oral, buccal, sublingual, inhalation, insufflation, or parenteral administration. However, for use in treating or preventing mucus hypersecretion in connection with smoking cessation, oral administration of the β-adrenergic inverse agonist is generally preferred. Other relevant routes of administration within the scope of the present invention include administration via a transdermal patch or as chewing gum.

If the β-adrenergic inverse agonist is administered orally, either in a conventional or a sustained-release preparation, it is typically administered in a conventional unit dosage form such as a tablet, a capsule, a pill, a troche, a wafer, a powder, or a liquid such as a solution, a suspension, a tincture, or a syrup. Oral formulations typically include such normally employed excipients as, for example, pharmaceutical grades of mannitol, lactose, starch, magnesium stearate, sodium saccharin, cellulose, magnesium carbonate, and other conventional pharmaceutical excipients. In certain defined embodiments, oral pharmaceutical compositions will comprise an inert diluent and/or assimilable edible carrier, and/or they may be enclosed in hard or soft shell gelatin capsules. Alternatively, they may be compressed into tablets. As another alternative, particularly for veterinary practice, they can be incorporated directly into food. For oral therapeutic administration, they can be incorporated with excipients or used in the form of ingestible tablets, buccal tablets, dragees, pills, troches, capsules, wafers, gums, or other conventional dosage forms.

The tablets, pills, troches, capsules, wafers, gums, or other conventional dosage forms can also contain the following: a binder, such as gum tragacanth, acacia, cornstarch, sorbitol, mucilage of starch, polyvinylpyrrolidone, or gelatin; excipients or fillers such as dicalcium phosphate, lactose, microcrystalline cellulose, or sugar; a disintegrating agent such as potato starch, croscarmellose sodium, or sodium starch glycolate, or alginic acid; a lubricant such as magnesium stearate, stearic acid, talc, polyethylene glycol, or silica; a sweetening agent, such as sucrose, lactose, or saccharin; a wetting agent such as sodium lauryl sulfate; or a flavoring agent, such as peppermint, oil of wintergreen, orange flavoring, or cherry flavoring. When the dosage unit form is a capsule, it can contain, in addition to materials of the above types, a liquid carrier. Various other materials can be present as coatings or to otherwise modify the physical form and properties of the dosage unit. For instance, tablets, pills, or capsules can be coated with shellac, sugar, or both. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes. One significant dosage forms is gums such as chewing gums; gum-forming agents and excipients are well known in the art. Chewing gums typically include natural or synthetic gum bases, colorings, flavorings, and other conventional ingredients.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In one alternative, a sustained-release formulation is used. Sustained-release formulations are well-known in the art. For example, they can include the use of polysaccharides such as xanthan gum and locust bean gum in conjunction with carriers such as dimethylsiloxane, silicic acid, a mixture of mannans and galactans, xanthans, and micronized seaweed, as recited in U.S. Pat. No. 6,039,980 to Baichwal, incorporated herein by this reference. Other sustained-release formulations incorporate a biodegradable polymer, such as the lactic acid-glycolic acid polymer recited in U.S. Pat. No. 6,740,634 to Saikawa et al., incorporated herein by this reference. Still other sustained-release formulations incorporate an expandable lattice that includes a polymer based on polyvinyl alcohol and polyethylene glycol, as recited in U.S. Pat. No. 4,428,926 to Keith, incorporated herein by this reference. Still other sustained-release formulations are based on the Eudragit™ polymers of Rohm & Haas, that include copolymers of acrylate and methacrylates with quaternary ammonium groups as functional groups as well as ethylacrylate methylmethacrylate copolymers with a neutral ester group. A particularly preferred extended release composition suitable for use in methods according to the present invention is an extended-release composition that contains nadolol or ICI-118,551 as its active ingredient.

Oral liquid preparations can be in the form of, for example, aqueous or oily suspensions, solutions, emulsions, syrups, tinctures, or elixirs, or can be presented as a dry product for reconstitution with water or other suitable vehicles before use. Such liquid preparations can contain conventional additives such as suspending agents, for example, sorbitol syrup, methylcellulose, glucose/sugar syrup, gelatin, hydroxymethylcellulose, carboxymethylcellulose, aluminum stearate gel, or hydrogenated edible fats; emulsifying agents, such as lecithin, sorbitan monooleate, or acacia; non-aqueous vehicles (which may include edible oils), for example, almond oil, fractionated coconut oil, oily esters, propylene glycol, or ethyl alcohol; or preservatives, for example, methylparaben, propylparaben, or sorbic acid. The preparations can also contain buffer salts, flavoring, coloring, or sweetening agents (e.g., mannitol) as appropriate.

One skilled in the art recognizes that the route of administration is an important determinant of the rate of efficiency of absorption. For example, the alimentary route, e.g., oral or buccal, is generally considered the safest route of administration. The delivery of the drugs into the circulation is slow, thus eliminating rapid high blood levels of the drugs that could potentially have adverse acute effects. Although this is considered the safest route of administration, there are several disadvantages. One important disadvantage is that the rate of absorption varies, which is a significant problem if a small range in blood levels separates a drug's desired therapeutic effect from its toxic effect, i.e., if the drug has a relatively low therapeutic index. Also, patient compliance is not always ensured, especially if oral administration is perceived by the patient as unpleasant. Furthermore, with oral administration, extensive hepatic metabolism can occur before the drug reaches its target site.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and/or mixtures thereof and/or in oils. Under ordinary conditions of storage and use, these preparations contain a preservative to prevent the growth of microorganisms. Suitable non-sensitizing and non-allergenic preservatives are well known in the art.

The carrier can also be a solvent and/or dispersion medium containing, for example, water, ethanol, a polyol (for example, glycerol, propylene glycol, and/or liquid polyethylene glycol, and/or the like), suitable mixtures thereof, and/or vegetable oils. The proper fluidity can be maintained for example, by the use of a coating, such as lecithin, by the maintenance of a suitable particle size in the case of a dispersion, and/or by the use of surfactants. The prevention of the action of microorganisms can be brought about by the inclusion of various antibacterial and/or antifungal agents, for example, parabens, chlorobutanol, phenol, sorbic acid, or thimerosal. In many cases it will be preferable to include isotonic agents, for example, sugars or sodium chloride. In many cases, it is preferable to prepare the solution in physiologically compatible buffers such as Hanks's solution, Ringer's solution, or physiological saline buffer.

Another route of administration of compositions according to the present invention is nasally, using dosage forms such as nasal solutions, nasal sprays, aerosols, or inhalants. Nasal solutions are usually aqueous solutions designed to be administered to the nasal passages in drops or sprays. Nasal solutions are typically prepared so that they are similar in many respects to nasal secretions, so that normal ciliary action is maintained. Thus, the aqueous nasal solutions usually are isotonic and/or slightly buffered in order to maintain a pH of from about 5.5 to about 6.5. In addition, antimicrobial preservatives, similar to those used in ophthalmic preparations, and/or appropriate drug stabilizers, if required, can be included in the formulation. Various commercial nasal preparations are known and can include, for example, antibiotics or antihistamines. Spray compositions can be formulated, for example, as aqueous solutions or suspensions or as aerosols delivered from pressurized packs, with the use of a suitable propellant, such as dichlorodifluoromethane, trichlorofluoromethane, dichlorotetrafluoroethane, 1,1,1,2,3,3,3-heptafluoropropane, 1,1,1,2-tetrafluoroethane, carbon dioxide, or other suitable gas.

Aerosol therapy allows an almost ideal benefit to risk ratio to be achieved because very small doses of inhaled medication provide optimal therapy with minimal adverse effects. However, the therapeutic efficiency of drugs administered by aerosolization depends not only on the pharmacological properties of the drugs themselves, but also on the characteristics of the delivery device. The characteristics of the delivery device influence the amount of drug deposited in the lungs and the pattern of drug distribution in the airways.

Aerosols are airborne suspensions of fine particles. The particles may be solids or liquids. Aerosol particles are heterodisperse (i.e. the particles are of a range of sizes) and aerosol particle size distribution is best described by a log normal distribution. Particles tend to settle (sediment), adhere to each other (coagulate), and adhere to structures such as tubing and mucosa (deposit). The particles delivered by aerosol can be conveniently characterized on the basis of their aerodynamic behavior. One parameter is the mass median aerodynamic diameter (MMAD). By definition, a particle distribution with an MMAD of 1 μm has the same average rate of settling as a droplet of unit density and 1 μm diameter.

The size of an aerosol particle, as well as variables affecting the respiratory system, influence the deposition of inhaled aerosols in the airways. On one hand, particles larger than 10 μm in diameter are unlikely to deposit in the lungs. However, particles smaller than 0.5 μm are likely to reach the alveoli or may be exhaled. Therefore, particles that have a diameter of between 1 μm and 5 μm are most efficiently deposited in the lower respiratory tract. Particles of these sizes are most efficient for the delivery of therapeutic agents, including β-adrenergic inverse agonists.

Therapeutic aerosols are commonly produced by atomization of liquids within jet nebulizers or by vibration of a standing pool of liquid (ultrasonic nebulization). Preformed aerosols may also be administered. Examples of the latter include MDIs and dry powder devices. Whatever delivery device is used, patients should be taught to use it correctly.

All jet nebulizers work via a similar operating principle, represented by the familiar perfume atomizer. A liquid is placed at the bottom of a closed container, and the aerosol is generated by a jet of air from either a compressor or a compressed gas cylinder passing through the device. Ultrasonic nebulizers produce an aerosol by vibrating liquid lying above a transducer at frequencies of about 1 mHz. This produces a cloud of particles that is carried out of the device to the patient by a stream of air. Aerosols varying in quantity, size and distribution of panicles can be produced by nebulizers, depending upon the design of the nebulizers and how it is operated. It should be noted that not all nebulizers have the required specifications (MMAD, flow, output) to provide optimum efficacy. A recent study compared the lung deposition from 4 nebulizers in healthy volunteers and showed that median lung aerosol deposition, expressed as percentages of the doses initially loaded into the nebulizers, ranged from 2 to 19%. To minimize adverse effects, pH and osmolarity of the nebulized solution should be controlled.

Metered dose inhalers (MDIs), because of their convenience and effectiveness, are probably the most widely used therapeutic aerosol used for inhaled drug delivery to outpatients. Most MDIs in current use contain suspensions of drug in propellant. There are 2 major components of an MDI: (i) the canister, a closed plastic or metal cylinder that contains propellant, active medication, and the metering chamber; and (ii) the actuator, a molded plastic container that holds the canister and directs the released aerosol towards the patient's airway.

Propellant mixtures are selected to achieve the vapor pressure and spray characteristics desired for optimal drug delivery. Chlorofluorocarbons were previously used, but non-chlorinated propellants are now employed because of environmental concerns. Finely divided particles of drug, usually less than 1 µm, are suspended in the pressurized (liquefied) propellant. To prevent the drug from coagulating, a surface active agent such as sorbitan oleate, lecithin or oleic acid is typically added; other surface active agents are known in the art. Metering chambers ordinarily contain 25 to 100 µL. The contents of the metering chamber are released when the canister is depressed into the actuator. Almost instantaneously, the propellants begin to evaporate, producing disintegration of the discharged liquid into particles that are propelled forward with great momentum. For optimal pulmonary drug deposition, the medication should be released at the beginning of a slow inspiration that lasts about 5 seconds and is followed by 10 seconds of breath-holding. Several inhalation aids have been designed to improve the effectiveness of a MDI. These are most useful in patients who have poor hand-to-breath coordination. A short tube (e.g. cones or spheres) may direct the aerosol straight into the mouth or collapsible bags may act as an aerosol reservoir holding particles in suspension for 3 to 5 seconds, during which time the patient can inhale the drug. However, when any of these devices is used, aerosol velocity upon entering the oropharynx is decreased and drug availability to the lungs and deposition in the oropharynx is decreased.

Dry powder inhalers have been devised to deliver agents to patients who have difficulty using an MDI (e.g. children and elderly patients). In general, the appropriate dosage is placed in a capsule along with a flow aid or filler such as large lactose or glucose particles. Inside the device, the capsule is initially either pierced by needles (e.g. Spinhaler®) or sheared in half (e.g. Rotohaler®). During inhalation the capsule rotates or a propeller is turned, creating conditions that cause the contents of the capsule to enter the inspired air and be broken up to small particles suitable for delivery to the airways. The energy required to disperse the powder is derived from the patient's inspiratory effort. Recently, more convenient multidose dry powder inhalers have been introduced (e.g. Diskhaler®, Turbuhaler®). Potential problems associated with dry powder inhalers include esophageal irritation and, consequently, cough due to the direct effect of powder in airways. Furthermore, the walls of the capsule may be coated with drug as a result of either failure of the capsule to release the drug or failure of the aggregated powder to break up. This may cause virtually all of the drug to be deposited in the mouth. These powder devices do not contain chlorofluorocarbons and may provide an alternative to MDIs.

Because of the nature of the interaction between inverse agonists and the β-adrenergic receptors with which they interact, the therapeutic response develops gradually over time as the receptor density in the affected tissues increases in response to the administration of inverse agonists. Typically, therefore, the inverse agonists are administered chronically over a considerable period of time. Therefore, in one particularly preferred alternative, the dosage is titrated at the start of administration with gradual increases. In other words, the β-adrenergic inverse agonist is administered over time in a series of graduated doses starting with the lowest dose and increasing to the highest dose. When the highest dose is reached, the β-adrenergic inverse agonist continues to be administered at that dose (the maintenance dose). For example, with nadolol administered orally, treatment can begin with 1 mg dosages, then progress through 3 mg, 5 mg, 10 mg, 15 mg, and then to higher maintenance dosages such as 25 mg, 30 mg, 50 mg, 75 mg, 100 mg, 150 mg or higher as deemed necessary, depending on the particular condition to be treated, the severity, and the response of the condition to the treatment. One particularly preferred dosage regimen begins at 10 mg, then progresses through 25, 50, 75, 100 and 150 mg based on defined dose escalation criteria determined by lung function, symptoms, heart rate, and blood pressure, as detailed further below. When the β-adrenergic inverse agonist is administered to treat or prevent mucus hypersecretion in a subject attempting smoking cessation, criteria related to the effect of the β-adrenergic inverse agonist treatment on the physiological state, mood, behavior, or craving of the subject for nicotine can also be included in the dose escalation calculation. Analogous dosing regimens can be used with other inverse agonists, the exact starting dose typically depending on the affinity of the inverse agonist for the binding site of the β-adrenergic receptor.

Various factors must be taken into account in setting suitable dosages for β-adrenergic inverse agonists. These factors include whether the patient is taking other medications that can alter the pharmacokinetics of the β-adrenergic inverse agonists, either causing them to be degraded more rapidly or more slowly. In particular, if the patient is taking the antibiotics erythromycin or neomycin, it is typically necessary to decrease the maintenance dose.

Toxicity and therapeutic efficacy of β-adrenergic inverse agonists can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture (i.e., the concentration of the test compound which achieves a half-maximal improvement in receptor signaling when chronic effects are considered). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps the dose frequency, will also vary according to the age, body weight, and response of the individual patient. A program comparable to that discussed above may be used in veterinary medicine as appropriate for conditions to which non-human mammals are subject and are treatable by administration of β-adrenergic inverse agonists.

Depending on the specific conditions being treated, such agents may be formulated and administered systemically or locally. Typically, administration is systemic. Techniques for formulation and administration may be found in Remington's Pharmaceutical Sciences, 18th ed., Mack Publishing Co., Easton, Pa. (1990). Suitable routes may include oral, oral controlled-release, nasal, buccal, or transdermal routes. Typically, oral administration is preferred, especially when a β-adrenergic inverse agonist is administered to treat or prevent mucus hypersecretion in a subject attempting smoking cessation. Buccal administration, using chewing gum, and transdermal administration, such as by the use of transdermal patches, are also significant routes of administration within the scope of the invention.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Methods for formulating compounds such as (1-adrenergic inverse agonists for transdermal administration are well known in the art and are described, for example, in K. D. Mccarley & A. L. Bunge, "Pharmacokinetic Models of Dermal Absorption," *J. Pharm. Sci.* 1699-1719 (2001) and in P. Morganti et al., "Percutaneous Absorption and Delivery Systems," *Clin. Dermatol.* 19: 489-501 (2001). In general, transdermal delivery systems involve incorporation of a medicament into a carrier such as a polymeric and/or a pressure-sensitive adhesive formulation or other forms of carriers. The pressure-sensitive adhesive must adhere effectively to the skin and permit migration of the active ingredient, such as a β-adrenergic inverse agonist from the carrier through the skin and into the bloodstream of the patient. Transdermal administration is described in U.S. Pat. No. 3,598,122 to Zaffaroni; U.S. Pat. No. 3,598,123 to Zaffaroni; U.S. Pat. No. 3,731,683 to Zaffaroni; U.S. Pat. No. 3,797,494 to Zaffaroni; U.S. Pat. No. 4,031,894 to Urquhart et al.; U.S. Pat. No. 4,144,317 to Higuchi et al.; U.S. Pat. No. 4,201,211 to Chandrasekaran et al.; U.S. Pat. No. 4,286,592 to Chandrasekaran; U.S. Pat. No. 4,314,557 to Chandrasekaran; U.S. Pat. No. 4,379,454 to Campbell et al.; U.S. Pat. No. 4,435,180 to Leeper; U.S. Pat. No. 4,559,222 to Enscore et al.; U.S. Pat. No. 4,568,343 to Leeper et al.; U.S. Pat. No. 4,573,995 to Chen et al.; U.S. Pat. No. 4,588,580 to Gale et al.; U.S. Pat. No. 4,645,502 to Gale et al.; U.S. Pat. No. 4,698,062 to Gale et al.; U.S. Pat. No. 4,704,282 to Campbell et al.; U.S. Pat. No. 4,725,272 to Gale; U.S. Pat. No. 4,781,924 to Lee et al.; U.S. Pat. No. 4,788,062 to Gale et al.; U.S. Pat. No. 4,816,258 to Nedberge et al.; U.S. Pat. No. 4,849,226 to Gale; U.S. Pat. No. 4,904,475 to Gale et al.; U.S. Pat. No. 4,908,027 to Enscore et al.; U.S. Pat. No. 4,917,895 to Lee et al.; U.S. Pat. No. 4,938,759 to Enscore et al.; U.S. Pat. No. 4,943,435 to Baker et al.; U.S. Pat. No. 5,004,610 to Osborne et al.; U.S. Pat. No. 5,071,656 to Lee et al.; U.S. Pat. No. 5,122,382 to Gale et al.; U.S. Pat. No. 5,141,750 to Lee et al.; U.S. Pat. No. 5,284,660 to Lee et al.; U.S. Pat. No. 5,314,694 to Gale et al.; U.S. Pat. No.

5,342,623 to Enscore et al.; U.S. Pat. No. 5,411,740 to Lee et al.; and U.S. Pat. No. 5,635,203 to Gale et al., all of which are incorporated herein by this reference.

Another route of administration that can be used is by the use of a chewing gum, a suitable route for buccal administration of the β-adrenergic inverse agonist. The use of chewing gum to administer pharmacologically active substances is well known in the art and is described, for example, in U.S. Pat. No. 7,101,579 to Athanikar et al.; U.S. Pat. No. 6,537,525 to West; U.S. Pat. No. 6,344,222 to Cherukuri et al.; U.S. Pat. No. 5,922,347 to Hausler et al.; and U.S. Pat. No. 4,971,079 to Talapin et al., all of which are incorporated herein by this reference.

Typically, in methods according to the present invention, the inverse agonist is administered in a daily dose or multiple times per day, depending on the half-life of the inverse agonist and on other factors described above. Alternatively, the inverse agonist can be administered less frequently, such as every other day, every third day, every fourth day, every week, and the like. Less frequent dosing may be achieved by the development of a depot of the drug in the body resulting in release of the drug over a sustained time period. This depot may be oral or injected. One skilled in the art of pharmacokinetics will recognize the importance of understanding the bioavailability and the half-life of a drug in relation to dosing of the particular drug. It is well known that a drug accumulates in the body if the time interval between doses is less than four of its half-lives, in which case, the total body stores of the drug are increased exponentially to a plateau or steady-state concentration. The average total body store of a drug at the plateau is a function of the dose, the interval between doses, the bioavailability of the drug, and the rate of the elimination of the drug. Thus, one of ordinary skill in the art is capable of determining the dose and interval of the dose for a given drug to achieve the desired effect.

Another embodiment of the present invention comprises a method of preventing or controlling mucus hypersecretion in the respiratory tract comprising administering to a subject with mucus hypersecretion or at risk of mucus hypersecretion:

(1) a therapeutically effective quantity of a β-adrenergic inverse agonist; and (2) a therapeutically effective quantity of an additional compound to treat mucus hypersecretion.

In this method, the subject with mucus hypersecretion or at risk of mucus hypersecretion can be a subject attempting to cease smoking.

The additional compound to treat mucus hypersecretion can be, but is not limited to, an antibiotic, a DNase, a bronchodilator, a corticosteroid, an expectorant, (2R,3R,4S,5R)-2-[6 amino-2-(1S-hydroxymethyl-2-phenyl-ethylamino)-purin-9-yl]-5-(2-ethyl-2H-tetrazol-5-yl)-tetrahydrofuran-3,4-diol, 4-hydroxy-7-[(2-[([2-[[3-(2-phenylethyoxy)propyl]sulfonyl]ethyl]amino]ethyl-2-(3H)-benzothiazolone, cis-20,4-cyano-4-[3-(cyclopentyloxy)-4-methoxyphenyl] cyclohexanecarboxylic acid, or a PDE4 inhibitor.

The antibiotic can be, but is not limited to: (1) an aminopenicillin, including, but not limited to, ampicillin and amoxacillin; (2) a quinolone, including, but not limited to, cinoxacin, norfloxacin, ciprofloxacin, ofloxacin, sparfloxacin, lomefloxacin, fleroxacin, pefloxacin, levofloxacin, trovafloxacin, gatifloxacin, moxifloxacin, clinafloxacin, and sitafloxacin; or (3) trimethoprimsulfamethoxazole.

The DNase can be, but is not limited to, recombinant human DNase.

The bronchodilator can be, but is not limited to, a methylxanthine, a sympathomimetic with strong $β_2$-adrenergic stimulating properties, or an anticholinergic. Methylxanthines include, but are not limited to, theophylline, aminophylline, theobromine, enprofylline, diprophylline, isbufylline, choline theophyllinate, albifylline, arofylline, bamifylline and caffeine. Sympathomimetics with $β_2$-adrenergic stimulating properties include, but are not limited to, albuterol, bitolterol, clenbuterol, clorprenaline, dobutamine, fenoterol, formoterol, isoetharine, isoprenaline, levabuterol, mabuterol, metaproterenol, pirbuterol, ritodrine, salbutamol, salmeterol, terbutaline, and the salts, solvates, analogues, congeners, bioisosteres, hydrolysis products, metabolites, precursors, and prodrugs thereof. Anticholinergics include, but are not limited to, ipratropium bromide, tiotropium bromide, and oxitropium bromide, and the salts, solvates, analogues, congeners, bioisosteres, hydrolysis products, metabolites, precursors, and prodrugs thereof.

Additionally, the additional compound can be a corticosteroid, including, but not limited to, beclomethasone, mometasone, budenoside, ciclesonide, flunisolide, fluticasone, methylprednisolone, prednisolone, prednisone, and triamcinolone, and the salts, solvates, analogues, congeners, bioisosteres, hydrolysis products, metabolites, precursors, and prodrugs thereof.

Additionally, the additional compound can be an epidermal growth factor receptor (EGF-R) antagonist, as described in U.S. Pat. No. 6,846,799 to Nadel et al., incorporated herein by this reference. Epidermal growth factor receptor antagonists include, but are not limited to: anti-EGF-R antibodies, tyrosine kinase inhibitors, antioxidants, inhibitors of mitogen-activated protein kinase kinase (MEK), inhibitors of transmembrane metalloproteinase (MP), and antibodies binding to factors that stimulate EGF production or EGF-R production. Particular inhibitors include tyrosine kinase inhibitors such as quinazolines, such as PD 153035, 4-β-chloroanilino) quinazoline, or CP-358,774; pyridopyrimidines; pyrimidopyrimidines; pyrrolopyrimidines, such as CGP 59326, CGP 60261 and CGP 62706, and pyrazolopyrimidines; 4-(phenylamino)7H-pyrrolo[2,3-d]pyrimidines; curcumin (diferuloyl methane); 4,5-bis(4-fluoroanilino)phthalimide; tyrphostins containing nitrothiophene moieties; the protein kinase inhibitor ZD-1839 (AstraZeneca); CP-358774 (Pfizer, Inc.); PD-0183805 (Warner-Lambert); or antisense molecules Additionally, the additional compound can be a PDE4 inhibitor, such as, but not limited to, cilomilast, filaminast, ibudilast, piclamilast, or roflumilast. Particularly preferred PDE4 inhibitors include roflumilast and cilomilast.

The β-adrenergic inverse agonist and the additional compound to treat mucus hypersecretion can be administered simultaneously or at different times. If the β-adrenergic inverse agonist and the additional compound are administered simultaneously, they can be administered in a single pharmaceutical composition or dosage form that includes both the β-adrenergic inverse agonist and the additional compound to treat mucus hypersecretion.

The mode of administration of the β-adrenergic inverse agonist and the additional compound to treat mucus hypersecretion can follow several different patterns. Examples of such patterns include the following: (1) The β-adrenergic inverse agonist and the additional compound to treat mucus hypersecretion are formulated together to give a single preparation which is administered. (2) The β-adrenergic inverse agonist and the additional compound to treat mucus hypersecretion are formulated into two different preparations which are administered concurrently by the same administration route, either simultaneously or close in time. (3) The β-adrenergic inverse agonist and the additional compound to treat mucus hypersecretion are formulated into two different preparations which are administered by the same administration route, but at different times. (4) The β-adrenergic inverse agonist and the additional compound to treat mucus hypersecretion are formulated into two different preparations which are administered concurrently by different administration routes, either simultaneously or close in time. (5) The β-adrenergic inverse agonist and the additional compound to treat mucus hypersecretion are formulated into two different preparations which are administered by different administration routes at different times, in either possible order of administration.

Pharmaceutical compositions and dosage forms that include both the β-adrenergic inverse agonist and the additional compound to treat mucus hypersecretion can be prepared according to methods well known in the art, such as those disclosed in U.S. Patent Application Publication No. 2005/0080113 by Ohkawa et al., incorporated herein by this reference.

Accordingly, various pharmaceutical compositions and dosage forms can be prepared including both the β-adrenergic inverse agonist and the additional compound to treat mucus hypersecretion as is generally known in the art. For example, the β-adrenergic inverse agonist and the additional compound to treat mucus hypersecretion can be mixed with a pharmacologically acceptable carrier to give pharmaceutical compositions, for example, tablets (including a sugar-coated tablet or film-coated tablet), powders, granules, capsules (including a soft capsule), solutions, sustained release agents and the like which can be safely administered orally.

Suitable pharmaceutically acceptable carriers are known in the art. For example, they can be conventional organic or inorganic carriers. Solid preparations can include excipient, lubricant, binder, and disintegrating agent. Liquid preparations can include solvents, solubilizing agents, suspending agents, agents that provide isotonicity, buffers, soothing agents, and other ingredients. Furthermore, additives such as conventional preservatives, antioxidants, colorants, sweetening agents, adsorbing agents, wetting agents and the like, can be used as appropriate and as generally known in the art.

Suitable excipients include, but are not limited to, lactose, sucrose, D-mannitol, starch, corn starch, microcrystalline cellulose, and light anhydrous silicic acid. Suitable lubricants include, but are not limited to, magnesium or calcium stearate, talc, and colloidal silica. Suitable binders include, but are not limited to, microcrystalline cellulose, sucrose, D-mannitol, dextrin, hydroxypropylcellulose, hydroxypropylmethylcellulose, polyvinylpyrrolidone, starch, saccharose, gelatin, methylcellulose, and sodium carboxymethylcellulose. Suitable disintegrating agents include, but are not limited to, starch, carboxymethylcellulose, calcium carboxymethylcellulose, sodium carboxymethylstarch, and L-hydroxypropylcellulose. Suitable solvents include, but are not limited to, water, alcohol, propylene glycol, macrogol sesame oil, corn oil, olive oil, soy oil, and other oils. Suitable solubilizing agents include, but are not limited to, glycol, propylene glycol, D-mannitol, benzyl benzoate, ethanol, tris-aminomethane, cholesterol, triethanolamine, sodium carbonate, and sodium citrate. Suitable suspending agents include, but are not limited to, surfactants such as stearyl triethenolamine, sodium lauryl sulfate, lauryl aminopropionate, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, and hydroxypropylcellulose. Suitable agents that provide isotonicity include, but are not limited to, glucose, D-sorbitol, sodium chloride, glycerol, and D-mannitol. Suitable buffers include, but are not limited to, phosphate buffer, acetate buffer, carbonate buffer, and citrate buffer. Suitable soothing agents include, but are not limited to, benzyl alcohol. Suitable preservatives include, but are not limited to, p-hydroxybenzoates, chlorobutanol, benzyl alcohol, phenethyl alcohol, dehydroacetic acid, and sorbic acid. Suitable antioxidants include, but are not limited to, sulfites, ascorbic acid, and α-tocopherol.

For preparations for oral administration including both the β-adrenergic inverse agonist and the additional compound to treat mucus hypersecretion, an excipient (e.g., lactose, sucrose, starch and the like), a disintegrating agent (e.g., starch, calcium carbonate and the like), a binder (e.g., starch, acacia, carboxymethylcellulose, polyvinylpyrrolidone, hydroxypropylcellulose and the like), a lubricant (e.g., talc, magnesium stearate, polyethylene glycol 6000 and the like) and the like, for example, can be added to the combination of the β-adrenergic inverse agonist and the additional compound, according to methods known in the art, and the mixture can be compression-molded, then if desirable, the molded product can be coated by conventional methods for the purposes of masking of taste, enteric property or durability, to obtain a preparation for oral administration. As this coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (methacrylic acid acrylic acid copolymer), pigment (e.g., iron oxide red, titanium dioxide, et.) or other conventional ingredients can be used. The preparation for oral administration can be a quick release preparation or a sustained release preparation.

The ratio of the β-adrenergic inverse agonist and the additional compound to treat mucus hypersecretion in a combination can be chosen depending on the route of administration, the clinical course of the patient, and the particular disease or condition being treated. As detailed above, in one embodiment of the invention, the disease or condition being treated is mucus hypersecretion associated with nicotine withdrawal in a subject attempting smoking cessation.

For example, the β-adrenergic inverse agonist and the additional compound to treat mucus hypersecretion can be made into a formulation suitable for aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin or other dispersing agents known in the art), a stabilizer (e.g., ascorbic acid, sodium pyrosulfite, or other stabilizers known in the art), a surfactant (e.g., Polysorbate 80, macrogol, or other surfactants known in the art), a solubilizer (e.g., glycerin, ethanol, or other solubilizers known in the art), a buffer (e.g., phosphoric acid/alkali metal salts thereof, citric acid/alkali metal salts thereof, or other buffers or buffer systems known in the art), an agent to provide isotonicity (e.g., sodium chloride, potassium chloride, mannitol, sorbitol, glucose, or other agents to provide isotonicity known in the art), a pH regulator (e.g., hydrochloric acid, sodium hydroxide, or other pH regulators known in the art), a preservative (e.g., ethyl p-hydroxybenzoate, benzoic acid, methylparaben, propylparaben, benzyl alcohol, or other preservatives known in the art), a dissolving agent (e.g., conc. glycerin, meglumine, or other dissolving agents known in the art), a dissolution aid (e.g., propylene glycol, sucrose, or other dissolution aids known in the art), a soothing agent (e.g., glucose, benzyl alcohol, or other soothing agents known in the art), or can be dissolved, suspended or emulsified in a vegetable oil such as olive oil, sesame oil, cotton seed oil, corn oil or other oils or a dissolution aid such as propylene glycol and molded into an oily formulation.

Accordingly, another aspect of the present invention is a pharmaceutical composition comprising:

(1) a therapeutically effective quantity of a β-adrenergic inverse agonist; and (2) at least one pharmaceutically acceptable carrier;

wherein the pharmaceutical composition is formulated to treat mucus hypersecretion.

Typically, this pharmaceutical composition is formulated to treat mucus hypersecretion associated with nicotine withdrawal.

Accordingly, yet another aspect of the present invention is a pharmaceutical composition comprising:

(1) a therapeutically effective quantity of a β-adrenergic inverse agonist;

(2) a therapeutically effective quantity of an additional compound to treat mucus hypersecretion; and (3) at least one pharmaceutically acceptable carrier;

wherein the pharmaceutical composition is formulated to treat mucus hypersecretion.

Typically, this pharmaceutical composition is formulated to treat mucus hypersecretion associated with nicotine withdrawal.

Yet another aspect of the present invention is a pharmaceutical composition comprising:

(1) a therapeutically effective quantity of a β-adrenergic inverse agonist;

(2) a therapeutically effective quantity of an additional compound to promote smoking cessation; and (3) at least one pharmaceutically acceptable carrier;

wherein the pharmaceutical composition is formulated to treat mucus hypersecretion associated with nicotine withdrawal.

The characteristics of the pharmaceutical composition, including the pharmaceutically acceptable carrier, the particular β-adrenergic inverse agonist used, the quantity of the β-adrenergic agonist, the particular additional compound to treat mucus hypersecretion, and the quantity of the additional compound to treat mucus hypersecretion, are as described above.

Typically, the pharmaceutical composition comprises a quantity of a β-adrenergic agonist and a quantity of an additional compound to treat mucus hypersecretion that are each therapeutically effective to treat mucus hypersecretion, especially the mucus hypersecretion associated with nicotine withdrawal in subjects attempting smoking cessation.

In another aspect of the invention, the β-adrenergic inverse agonist can be administered to a subject attempting smoking cessation along with one or more additional compounds to promote smoking cessation. In contrast to the additional compound to treat mucus hypersecretion described above, the additional compound to promote smoking cessation does not treat mucus hypersecretion directly; its pharmacological activity is directed to another physiological or psychological process impacted by cigarette smoking. Such additional compounds to promote smoking cessation include, but are not limited to, buproprion, varenicline, clonidine, and nortriptyline, and the salts, solvates, analogues, congeners, mimetics, bioisosteres, stereoisomers, hydrolysis products, metabolites, precursors, and prodrugs thereof.

Accordingly, when one or more additional compounds to promote smoking cessation are employed, another aspect of the invention is a method of preventing or controlling mucus hypersecretion in the respiratory tract in a subject attempting smoking cessation who is at risk for mucus hypersecretion comprising administering to the subject:

(1) a therapeutically effective quantity of a β-adrenergic inverse agonist; and (2) a therapeutically effective quantity of an additional compound to promote smoking cessation.

Similarly, when one or more additional compounds to promote smoking cessation are employed, a pharmaceutical composition according to the present invention can comprise:

(1) a therapeutically effective quantity of a β-adrenergic inverse agonist as described above;

(2) a therapeutically effective quantity of an additional compound to promote smoking cessation as described above; and (3) at least one pharmaceutically acceptable carrier.

It is also possible to prepare a pharmaceutical composition that includes both: (i) at least one additional compound to treat mucus hypersecretion as described above; and (ii) at least one additional compound to promote smoking cessation as described above. Therefore, in this alternative, such a pharmaceutical composition can comprise:

(1) a therapeutically effective quantity of a β-adrenergic inverse agonist as described above;

(2) a therapeutically effective quantity of an additional compound to treat mucus hypersecretion as described above;

(3) a therapeutically effective quantity of an additional compound to promote smoking cessation as described above; and (4) at least one pharmaceutically acceptable carrier.

In pharmaceutical compositions according to the present invention, it is possible to include more than one β-adrenergic inverse agonist, more than one additional compound to treat mucus hypersecretion (if present), and more than one additional compound to promote smoking cessation (if present) in the pharmaceutical composition. However, for most purposes, it is generally preferred to include only one β-adrenergic inverse agonist, only one additional compound to treat mucus hypersecretion (if present), and only one compound to promote smoking cessation (if present) in the pharmaceutical composition.

When both an additional compound to treat mucus hypersecretion and an additional compound to promote smoking cessation are employed, a method of preventing or controlling mucus hypersecretion in the respiratory tract in a subject attempting smoking cessation who is at risk for mucus hypersecretion comprising administering to the subject:

(1) a therapeutically effective quantity of a β-adrenergic inverse agonist;

(2) a therapeutically effective quantity of an additional compound to treat mucus hypersecretion; and (3) a therapeutically effective quantity of an additional compound to promote smoking cessation.

When an additional compound to promote smoking cessation, or both an additional compound to treat mucus hypersecretion and an additional compound to promote smoking cessation are administered to a subject attempting smoking cessation, the same general principles apply with respect to the dosages, dosage frequencies, and routes of administration as when the β-adrenergic inverse agonist and the additional compound to treat mucus hypersecretion are administered to such a subject as described above. The β-adrenergic inverse agonist and the compound to promote smoking cessation can be administered at the same time or at different times. If all three of: (i) the β-adrenergic inverse agonist; (ii) the additional compound to treat mucus hypersecretion; and (iii) the additional compound to treat smoking cessation are administered, these three compounds can be administered at the same time, or two of the compounds can be administered at one time and the third administered at a different time, or all three of the compounds can be administered at different times. A variety of schedules would be known to one of ordinary skill in the art and thus would be within the scope of the present invention. Similarly, the mode of administration of the β-adrenergic inverse agonist, the additional compound to promote smoking cessation, and the additional compound to treat mucus hypersecretion, if used, can follow a number of different patterns. If only two compounds are used (i.e., the β-adrenergic inverse agonist and the additional compound to promote smoking cessation), the patterns of administration can be analogous to those described above with respect to the patterns of administration when the β-adrenergic inverse agonist and the additional compound to treat mucus hypersecretion are used, with the additional compound to promote smoking cessation replacing the additional compound to treat mucus hypersecretion in the patterns of administration described above. When all three compounds are used (i.e., the β-adrenergic inverse agonist, the additional compound to treat mucus hypersecretion, and the additional compound to promote smoking cessation), all possible patterns of administration are within the scope of the invention as to the time of administration, route of administration, simultaneity of administration of more than one compound, and the use of preparations including one or more than one compound for administration.

The invention is illustrated by the following Example. This Example is included for illustrative purposes only, and is not intended to limit the invention.

EXAMPLE

Reversal of Transformation of Lung Airways from Ciliated Epithelium to Mucus Producing Epithelium after Chronic Inverse Agonist Treatment Mice were made asthmatic by sensitization to the antigen ovalbumin. Balb/cJ mice aged 6 weeks (Jackson Animal Laboratory, Bar Harbor, Me.) were housed under specific pathogen-free conditions and fed a chicken ovalbumin-free diet. Mice were sensitized with subcutaneous injection of 25 µg of ovalbumin adsorbed to aluminum hydroxide on protocol days 2, 9, and 16. Subsequently, mice were given 504 of saline solution containing 25 µg of ovalbumin intranasally, on a daily basis, from protocol days 23 through 27. A group of ovalbumin-sensitized saline-challenged mice serves as controls for systemic sensitization and respiratory challenges with ovalbumin. Prior to intranasal administrations, mice were sedated with halothane vapor. For the study of this Example, ovalbumin-sensitized and ovalbumin-challenged mice, and ovalbumin-sensitized and saline-challenged mice will be referred to as asthmatic mice and control mice, respectively.

Animals received drug treatment for 7 days from day 21 to 27 of the sensitization/challenging protocol; ICI-118,551 at 10 mg/kg, was administered 3 times a day subcutaneously by osmotic minipump (Alzet®, #2004, Durect Corporation, Cupertino, Calif.). ICI-118,551 was dissolved in 50% DMSO.

After BALF (bronchoalveolar lavage fluid) and blood were taken, lungs were: (1) perfused with 4% paraformaldehyde through the cannula, then washed with PBS thrice; (2) put into 30% sucrose/PBS until all the tissue went down to the bottom of the tubes; (3) the medial section of the left lung was then used for cryosectioning. For cryosectioning: (1) lungs were taken from sucrose solution and transferred onto a small Petri dish; (2) on a mold a thin film of OCT medium was made and placed on a surface of the container tightly packed with dry ice; (3) before the OCT medium solidification, the tissue was placed on it in an upright position holding it with a forceps (the position of tissue placement can be manipulated according to the section required); (4) once the block was ready it was stored at −80° C. until use; (5) then sections of 12 µm thickness were made and collected on the slides.

Figure 3:
FIG. 3 is a photomicrograph of a section from lung tissue of asthmatic mice chronically treated with the β-adrenergic inverse agonist ICI 118,551; staining is with hematoxylin-eosin.
Figure 4:
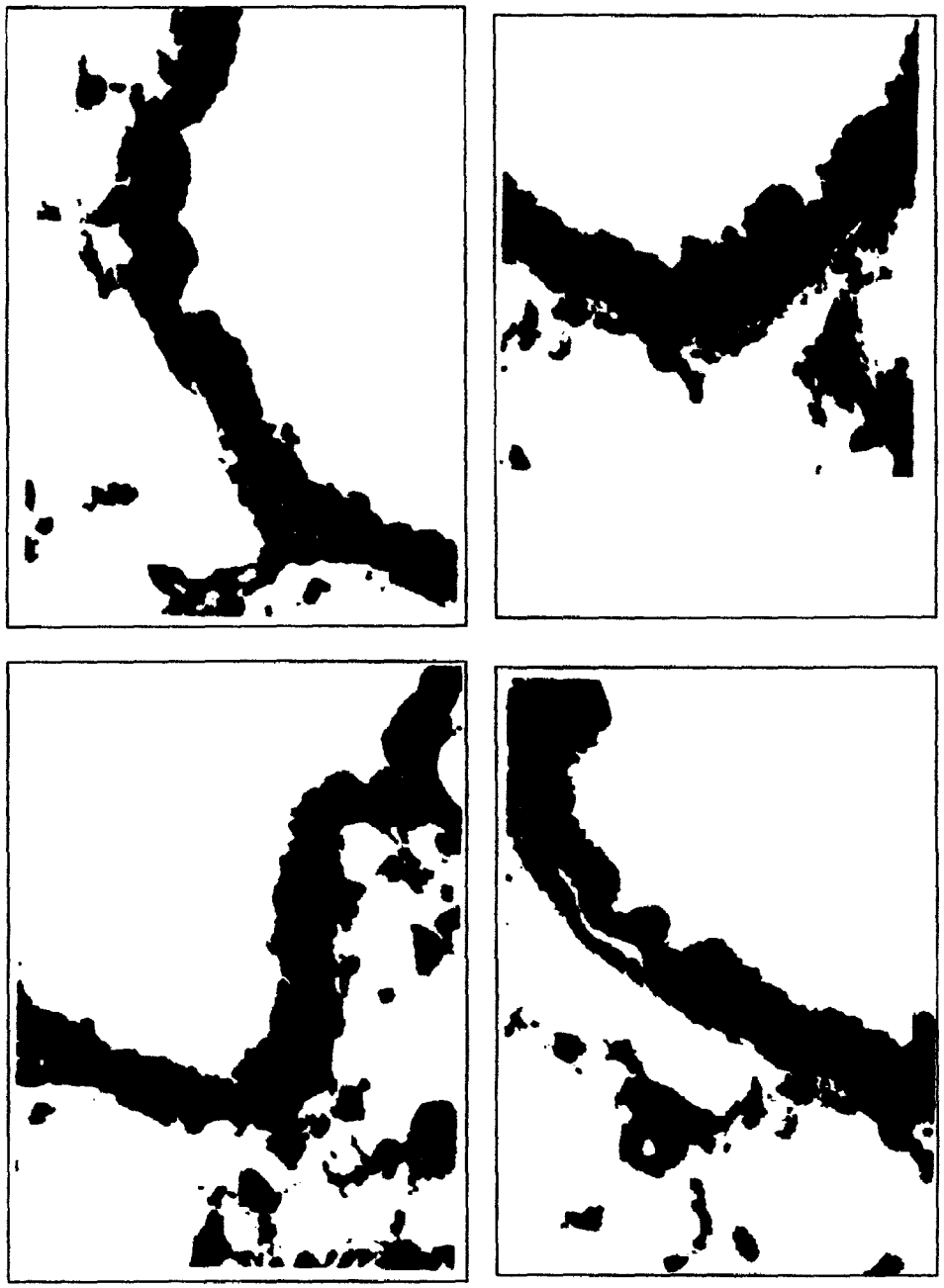
FIG. 4 is a photomicrograph of a section from lung tissue of control mice stained with periodic acid-Schiff (PAS) stain; the epithelial cells mostly are not stained.
Figure 5:
FIG. 5 is a photomicrograph of a section from lung tissue of asthmatic mice stained with PAS stain; the epithelium has mostly been converted to goblet cells which secrete mucus.
Figure 6:
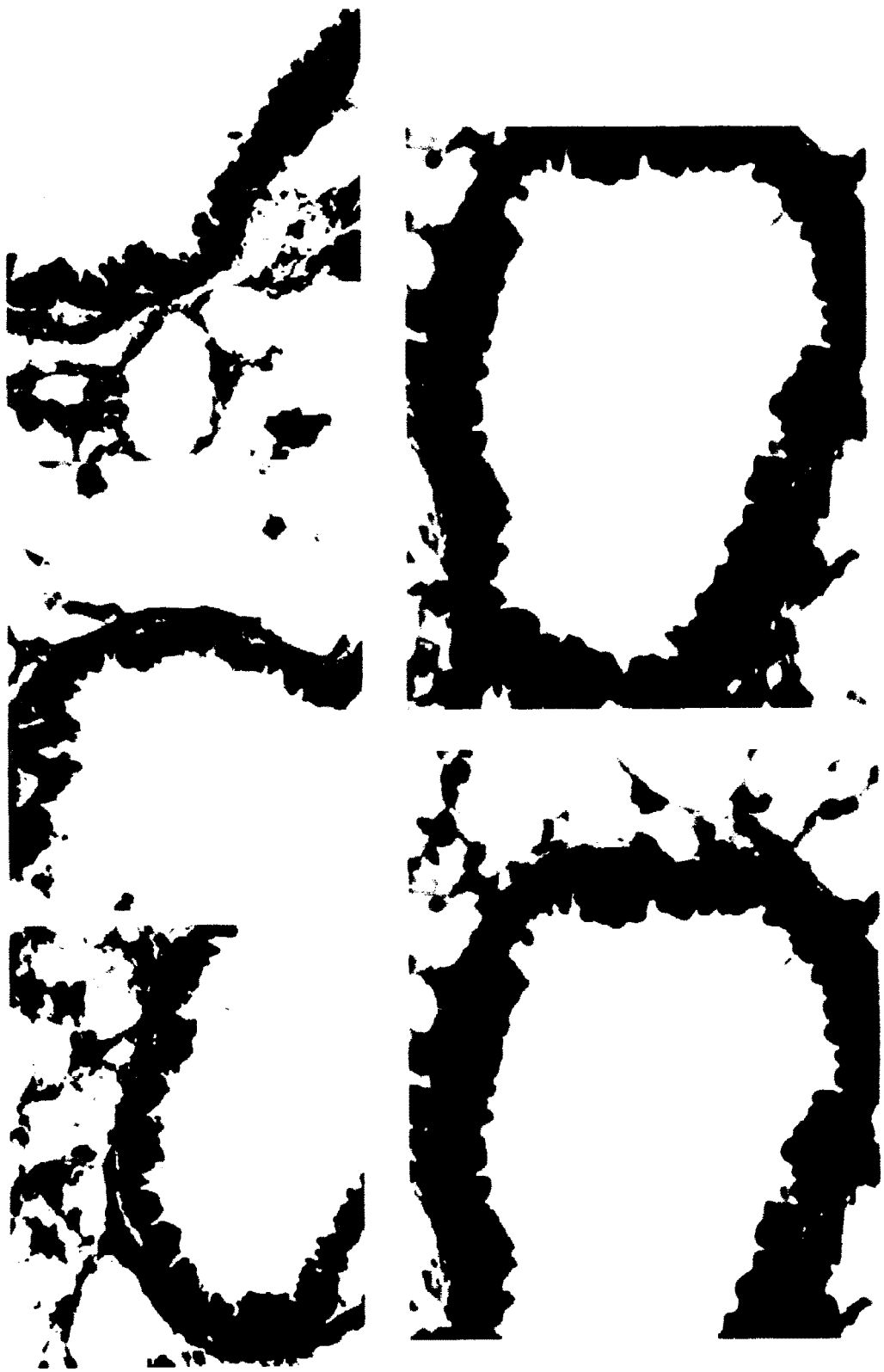
FIG. 6 is a photomicrograph of a section from lung tissue of asthmatic mice chronically treated with the β-adrenergic inverse agonist ICI 118,551 stained with PAS stain; the epithelial cells appear substantially normal.

Lungs were then stained with hematoxylin-eosin (FIGS. 1-3) or with periodic acid-Schiff stain (FIGS. 4-6). Hematoxylin and eosin staining was performed as follows: While sections were in water, surface was skimmed of hematoxylin with a Kimwipe to remove oxidized particles. Excess water was blotted from slide holder before going into hematoxylin. For hematoxylin staining, staining was carried out 1×3 minutes with hematoxylin; slides were washed with distilled water, and then 1×5 minutes with tap water to allow the stain to develop. The slides were then dipped 8-12× rapidly in acid ethanol to destain. Slides were then washed 2×1 minutes in tap water and 1×2 minutes in deionized water. Excess water was blotted from the slide holder before going into eosin. For eosin staining and dehydration, excess water was blotted from the slide holder before going into eosin. Eosin staining was performed for 1×30 sec in eosin (up to 45 seconds for an older batch of eosin, then 3×5 minutes 95% ethanol, 3×5 minutes 95% ethanol, 3×5 minutes 100% ethanol (excess ethanol was blotted before going into xylene), and finally 3×15 minutes in xylene. Slides were left in xylene overnight to get good clearing of any water. Coverslips were mounted using Permount. Slides were dried overnight in the hood. For staining with periodic acid-Schiff stain, after standard tissue preservation and embedding in OCT, slides were: (1) placed in 0.5% periodic acid for 5 minutes; (2) rinsed in distilled water; (3) embedded in Schiff's Reagent at room temperature for 30 minutes; (4) washed in running tap water for 5 minutes; (5) counterstained in hematoxylin for 3 minutes; (6) washed in distilled water; (7) treated for 3×5 minutes in 95% alcohol; (8) treated for 3×5 minutes in 100% alcohol; (9) treated for 3×5 minutes with xylene; and (10) completed by placing a coverslip after a drop of mounting medium was placed on the slide.

FIG. 1 is a photomicrograph of a section from lung tissue of control mice showing normal epithelium; staining is with hematoxylin-eosin. These are mostly ciliated cells but cilia have not been preserved.

Figure 2:
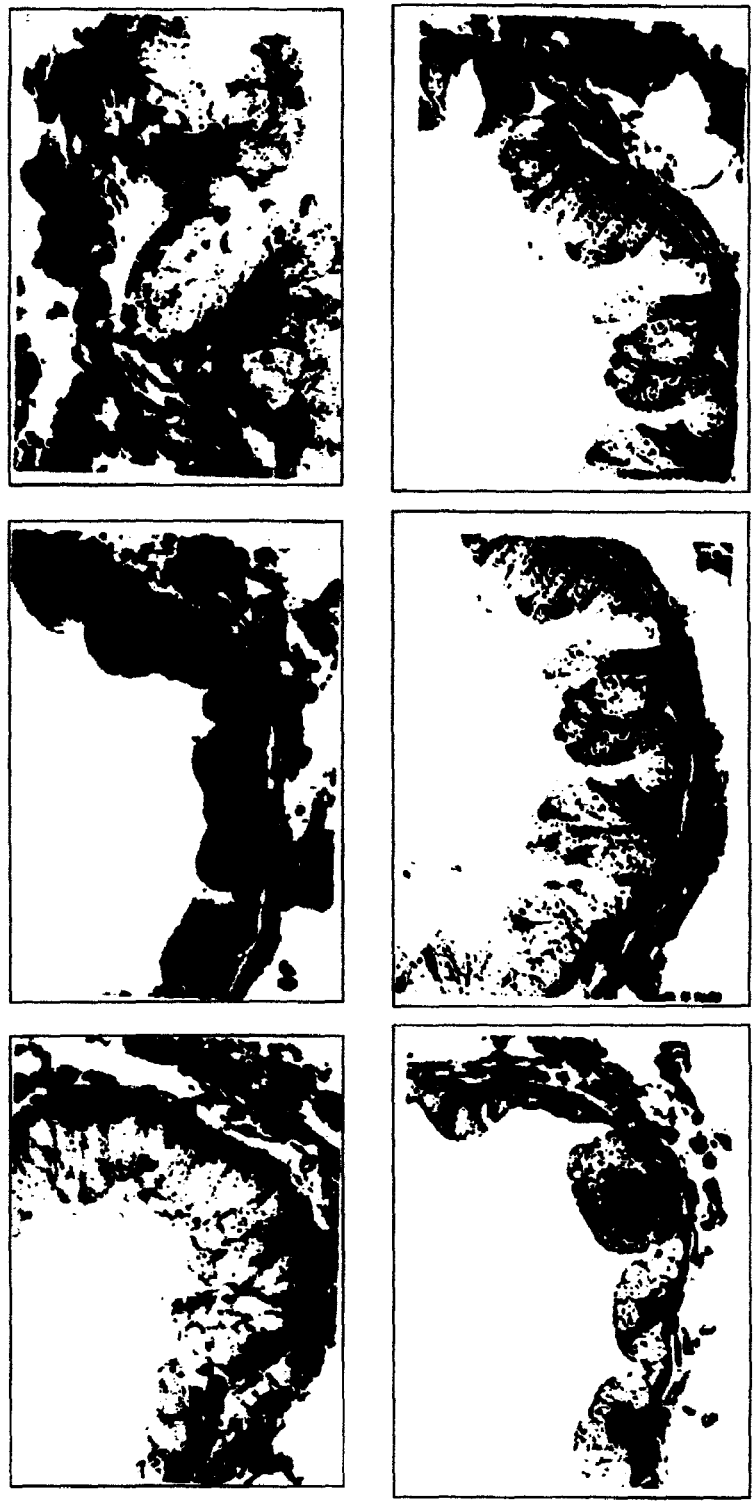
FIG. 2 is a photomicrograph of a section from lung tissue of asthmatic mice showing changes in the epithelium; staining is with hematoxylin-eosin.

FIG. 2 is a photomicrograph of a section from lung tissue of asthmatic mice showing significant changes in the epithelium; staining is with hematoxylin-eosin.

FIG. 3 is a photomicrograph of a section from lung tissue of asthmatic mice chronically treated with the β-adrenergic inverse agonist ICI 118,551; staining is with hematoxylin-eosin. The epithelial cells have substantially returned to their normal appearance.

FIG. 4 is a photomicrograph of a section from lung tissue of control mice stained with periodic acid-Schiff (PAS) stain. The epithelial cells mostly are not stained.

FIG. 5 is a photomicrograph of a section from lung tissue of asthmatic mice stained with PAS stain. The epithelium has mostly been converted to goblet cells which secrete mucus.

FIG. 6 is a photomicrograph of a section from lung tissue of asthmatic mice chronically treated with the β-adrenergic inverse agonist ICI 118,551 stained with PAS stain. The epithelial cells appear substantially normal.

In the animal asthma model employed in this Example the airway epithelium differs from normal epithelium in that there is a proliferation of mucus secretory cells resulting in mucus hypersecretion. Additionally there is a deficiency of ciliated epithelium resulting in an impairment of normal mucociliary clearance. Chronic treatment with the $β_2$ selective inverse agonist ICI 118,551 restores the airway epithelium to a normal healthy state by reducing the secretory cells thereby reversing mucus hypersecretion.

The results of FIGS. 1-6 establish that chronic administration of the β-adrenergic inverse agonist ICI 118,551 to asthmatic mice substantially reversed the transformation of lung epithelium from primarily ciliated cells to goblet cells that produced mucus, so that the appearance of the lung epithelial cells was substantially normal after inverse agonist treatment. This result strongly supports the hypothesis that administration of a β-adrenergic inverse agonist reduces the hypersecretion of mucus and thus is of value for the treatment of diseases and conditions characterized by epithelial airway (nasal and pulmonary) hypersecretion of mucus. This results also strongly supports the hypothesis that administration of a β-adrenergic inverse agonist can significantly assist a subject attempting smoking cessation, inasmuch as mucus hypersecretion is one of the most important physiological consequences of smoking cessation and is frequently responsible for failure of the subject to refrain from smoking.

ADVANTAGES OF THE INVENTION

The present invention provides an improved method of preventing or reversing the hypersecretion of mucus, particularly in the respiratory system, and of treating diseases and conditions characterized by the hypersecretion of mucus, including, but not limited to chronic cough, chronic cough associated with productive cough, chronic cough associated with non-productive cough and chronic bronchitis. The method is particularly suitable for subjects attempting smoking cessation, inasmuch as mucus hypersecretion is one of the most significant consequences of smoking cessation and the resulting discomfort drives many subjects who attempt to quit smoking to resume smoking. The method is well adapted to regular use and prevents the development of resistance or unresponsiveness to agents that might otherwise treat hypersecretion. The method actually reverses the transformation of ciliated epithelium of the respiratory system to epithelium dominated by mucus-secreting goblet cells. The method is well tolerated and does not result in side effects; it can be used together with other conventional therapeutic modalities for diseases or conditions characterized by mucus hypersecretion. In particular, methods of administration of β-adrenergic inverse agonists according to the present invention address one or more of the physiological symptoms associated with smoking cessation, including, but not limited to, tremor, mucus hypersecretion, and cough. This activity provides a unique approach to smoking cessation and complements other methods that treat psychological and behavioral issues.

The methods and compositions described herein possess industrial applicability for the preparation of a medicament for the treatment of mucus hypersecretion, especially in connection with smoking cessation, but not limited thereto.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

We claim:

1. A method of preventing or controlling mucus hypersecretion in the respiratory tract comprising administering a therapeutically effective quantity of a β-adrenergic inverse agonist to a subject with mucus hypersecretion for a period required to increase the likelihood of the subject quitting smoking, wherein the mucus hypersecretion is associated with smoking cessation and the subject is attempting smoking cessation, wherein the method increases the likelihood of the subject quitting smoking and prevents or reduces at least one of the anatomical or physiological changes causing symptoms associated with smoking cessation, and wherein the β-adrenergic inverse agonist is a $β_2$-selective inverse agonist selected from the group consisting of nadolol, carvedilol, and ICI-118,551, wherein the prevention or control of mucus hypersecretion increases the likelihood of the subject quitting smoking and wherein a chronic administration of a β-adrenergic inverse agonist has the effect of upregulating the population of active β-adrenergic receptors.

2. The method of claim 1 wherein the β-adrenergic inverse agonist is nadolol.

3. The method of claim 1 wherein the β-adrenergic inverse agonist is carvedilol.

4. The method of claim 1 wherein the method exerts a therapeutic effect that is an upregulation of pulmonary β-adrenergic receptors.

5. The method of claim 1 wherein the method inhibits or reverses the transformation of epithelial cells of the respiratory tract into mucus-producing goblet cells.

6. The method of claim 1 wherein the β-adrenergic inverse agonist is administered by use of a transdermal patch or by chewing gum.

7. The method of claim 1 wherein the method further treats one or more symptoms selected from the group consisting of tremor and cough.

8. A method of treating or preventing a disease or condition characterized by mucus hypersecretion comprising administering a therapeutically effective quantity of a β-adrenergic inverse agonist to a subject with such a disease or condition for a period required to increase the likelihood of the subject quitting smoking, wherein the method increases the likelihood of the subject quitting smoking and prevents or reduces at least one of the anatomical or physiological changes causing symptoms associated with smoking cessation, and wherein the β-adrenergic inverse agonist is a $β_2$-selective inverse agonist selected from the group consisting of nadolol, carvedilol, and ICI-118,551, wherein the treatment or prevention of the disease or condition characterized by mucus hypersecretion increases the likelihood of the subject quitting smoking and wherein a chronic administration of a β-adrenergic inverse agonist has the effect of upregulating the population of active β-adrenergic receptors.

9. The method of claim 8 wherein the disease or condition is nicotine withdrawal.

10. The method of claim 8 wherein the method further treats one or more symptoms selected from the group consisting of tremor and cough.

11. A method of preventing or controlling mucus hypersecretion in the respiratory tract comprising administering to a subject with mucus hypersecretion or at risk of mucus hypersecretion:
   (a) a therapeutically effective quantity of a β-adrenergic inverse agonist; and
   (b) a therapeutically effective quantity of an additional compound to treat mucus hypersecretion, wherein the mucus hypersecretion is associated with smoking cessation and the subject is attempting smoking cessation, wherein the method increases the likelihood of the subject quitting smoking and prevents or reduces at least one of the anatomical or physiological changes causing symptoms associated with smoking cessation, and wherein the β-adrenergic inverse agonist is a 132-selective inverse agonist selected from the group consisting of nadolol, carvedilol, and ICI-118,551, wherein the prevention or control of mucus hypersecretion increases the likelihood of the subject quitting smoking, and wherein the β-adrenergic inverse agonist is administered for a period that is required to increase the likelihood of the subject quitting smoking and wherein a chronic administration of a β-adrenergic inverse agonist has the effect of upregulating the population of active β-adrenergic receptors.

12. The method of claim 11 wherein the β-adrenergic inverse agonist is nadolol.

13. The method of claim 11 wherein the β-adrenergic inverse agonist is carvedilol.

14. The method of claim 11 wherein the additional compound to treat mucus hypersecretion is selected from the group consisting of an antibiotic; a DNase; a bronchodilator; a corticosteroid; an epidermal growth factor receptor antagonist; an expectorant; 4-hydroxy-7-[2-[[2-[[3-(2-phenylethyoxy)propyl]sulfonyl]ethyl]amino]ethyl-2-(3H)-benzothiazolone; cis-20,4-cyano-4-[3-(cyclopentyloxy)-4-methoxyphenyl]cyclohexanecarboxylic acid; and a PDE4 inhibitor.

15. A method of preventing or controlling mucus hypersecretion in the respiratory tract comprising administering to a subject with mucus hypersecretion, wherein the mucus hypersecretion is associated with smoking cessation and the subject is attempting smoking cessation:
   (a) a therapeutically effective quantity of a β-adrenergic inverse agonist; and
   (b) a therapeutically effective quantity of an additional compound to promote smoking cessation, wherein the mucus hypersecretion is associated with smoking cessation and the subject is attempting smoking cessation, wherein the method increases the likelihood of the subject quitting smoking and prevents or reduces at least one of the anatomical or physiological changes causing symptoms associated with smoking cessation, and wherein the β-adrenergic inverse agonist is a $β_2$-selective inverse agonist selected from the group consisting of nadolol, carvedilol, and ICI-118,551, wherein the prevention or control of mucus hypersecretion increases the likelihood of the subject quitting smoking, and wherein the β-adrenergic inverse agonist is administered for a period that is required to increase the likelihood of the subject quitting smoking and wherein a chronic administration of a β-adrenergic inverse agonist has the effect of upregulating the population of active β-adrenergic receptors.

16. The method of claim 15 wherein the β-adrenergic inverse agonist is nadolol.

17. The method of claim 15 wherein the β-adrenergic inverse agonist is carvedilol.

18. The method of claim 15 wherein the additional compound to promote smoking cessation is selected from the group consisting of buproprion, varenicline and nortriptyline.

* * * * *